US008106033B2

(12) United States Patent
Reddy et al.

(10) Patent No.: US 8,106,033 B2
(45) Date of Patent: Jan. 31, 2012

(54) COMPOSITION AND METHODS FOR THE TREATMENT OF PROLIFERATIVE DISEASES

(75) Inventors: E. Premkumar Reddy, Villanova, PA (US); James F. Holland, Scarsdale, NY (US)

(73) Assignees: Temple University - Of The Commonwealth System of Higher Education, Philadelphia, PA (US); Mount Sinai School of Medicine, New York, NY (US)

( * ) Notice: Subject to any disclaimer, the term of this patent is extended or adjusted under 35 U.S.C. 154(b) by 540 days.

(21) Appl. No.: 11/885,770

(22) PCT Filed: Mar. 10, 2006

(86) PCT No.: PCT/US2006/008704
§ 371 (c)(1),
(2), (4) Date: Sep. 6, 2007

(87) PCT Pub. No.: WO2006/104668
PCT Pub. Date: Oct. 5, 2006

(65) Prior Publication Data
US 2008/0161252 A1    Jul. 3, 2008

Related U.S. Application Data

(60) Provisional application No. 60/660,784, filed on Mar. 11, 2005.

(51) Int. Cl.
| A61K 31/661 | (2006.01) |
| A61K 31/10  | (2006.01) |
| A61K 31/164 | (2006.01) |
| A61K 31/18  | (2006.01) |
| A61K 31/215 | (2006.01) |
| A61K 31/255 | (2006.01) |

(52) U.S. Cl. ............. 514/127; 514/239.2; 514/506; 514/532; 514/601; 514/613; 514/708; 514/709; 514/710

(58) Field of Classification Search .............. 514/127, 514/239.2, 506, 532, 601, 613, 708, 709, 514/710
See application file for complete search history.

(56) References Cited

U.S. PATENT DOCUMENTS

| 6,486,210 | B2  | 11/2002 | Reddy et al. ............ 514/708 |
| 6,667,346 | B2  | 12/2003 | Reddy et al. ............ 514/710 |
| 6,767,926 | B1  | 7/2004  | Cosenza et al. |
| 7,595,347 | B2  | 9/2009  | Cosenza et al. ........... 514/710 |
| 7,598,232 | B2* | 10/2009 | Reddy et al. ............ 514/114 |
| 2005/0014725 | A1* | 1/2005 | Mi et al. ............... 514/80 |
| 2005/0130942 | A1  | 6/2005 | Reddy et al. |
| 2006/0280746 | A1  | 12/2006 | Reddy et al. ........... 424/155.1 |
| 2008/0058290 | A1  | 3/2008 | Reddy et al. ........... 514/127 |

FOREIGN PATENT DOCUMENTS

| WO | WO 03/072062 A2 | 9/2003 |
| WO | WO 2005/065074 | * 7/2005 |
| WO | WO 2005/089269 | * 9/2005 |

OTHER PUBLICATIONS

U.S. Appl. No. 12/310,575, filed Aug. 30, 2006, Reddy et al.
U.S. Appl. No. 11/794,524, filed Jun. 28,2007, Reddy et al.
U.S. Appl. No. 12/460,182, filed Jul. 14, 2009, Reddy et al.
J.-D. Jiang, et al., "Anticancer Effects of ON-1910Na", Abstract #5382, AACR 95th Annual Meeting, Mar. 27-31, 2004.
Press Release, "Onconova Therapeutics Begins Phase I Clinical Trial of Anti-Cancer Agent", Jul. 26, 2004.
A.K. Sharma, et al., "Radiation Sensitization of Prostate Carcinoma Cells by One 01910, A Novel Protein Kinase Inhibitor and Cell Cycle Modulator", Abstract #2003, ASTRO 46th Annual Meeting, Oct. 3-7, 2004.
K. Gumireddy, et al., "A non-ATP-competitive inhibitor of BCR-ABL overrides, imatinib resistance", *Proc. Nat. Acad. Sci.*, USA, 2005, 102, 1992 (Feb. 8, 2005).
K. Gumireddy, et al., "ON01910, a non-ATP-competitive small molecule inhibitor of Plk1, is a potent anticancer agent", *Cancer Cell*, 2005, 7, 275-86.
S. Mohan, et al., "Selective Radiosensitization and Cell Cycle Modulation in Prostate Carcinoma Cells by ON10910, A Novel Benzyl Styrene Sulfone", Abstract #2005, AACR 96th Annual Meeting, Apr. 16-20, 2005.
T. Ohnuma, et al., "Influence of Human Serum Albumin on Cytotoxic Activity of ON01910.Na", Abstract #4103, AACR 96th Annual Meeting, AACR 96th Annual Meeting, Apr. 16-20, 2005.
J. Roboz, et al., Cellular "Uptake of Benzyl Styryl Sulfone 1910Na in Cell Cultures and its Complexing with Human Serum Albumin", Abstract #4838, AACR 96th Annual Meeting, AACR 96th Annual Meeting, Apr. 16-20, 2005.
J. Jiang, et al., "Effects of ON1910.Na in Combination Chemotherapy", Abstract #4993, AACR 96th Annual Meeting, AACR 96th Annual Meeting, Apr. 16-20, 2005. (We also have the poster for this presentation).
A. Preda, et al., "Cytotoxic Effect of ON01910.Na in Combination with Cisplatin, Flavopiridol, Doxorubicin and other Antitumor Agents in Vitro", Abstract #5008, AACR 96th Annual Meeting, AACR 96th Annual Meeting, Apr. 16-20, 2005.

(Continued)

*Primary Examiner* — Jason Sims
*Assistant Examiner* — Zohreh Vakili
(74) *Attorney, Agent, or Firm* — Drinker Biddle & Reath LLP

(57) ABSTRACT

Methods and compositions are provided for treating proliferative disorders, wherein the composition comprises at least one compound according to Formula I:

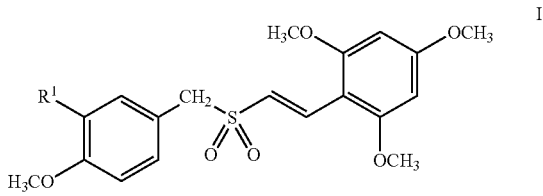

wherein $R^1$ is selected from the group consisting of —OH, —NH$_2$, —NH—CH$_2$—CO$_2$H, —NH—CH(CH$_3$)—CO$_2$H, and —NH—C(CH$_3$)$_2$—CO$_2$H, or a pharmaceutically acceptable salt of such a compound; and an anthracycline, e.g. doxorubicin, or a pharmaceutically acceptable salt thereof, or a platin, e.g. oxaliplatin, or a pharmaceutically acceptable salt thereof.

18 Claims, 4 Drawing Sheets

OTHER PUBLICATIONS

A. Danish, et al.,"Cytotoxicity and Radiosensitization in Cervical Carcinoma Cells by ON01910, a Novel Polio-Like Kinase 1 Inhibitor", ASTRO 47th Annual Meeting, Oct. 16-20, 2005.

W.S. el-Deiry, "Meeting Report: The International Conference on Tumor Progression and Therapeutic Resistance", *Cancer Res.*, 2005, 65(11), 4475-84.

* cited by examiner

COMPOSITION AND METHODS FOR THE TREATMENT OF PROLIFERATIVE DISEASES

CROSS-REFERENCE TO RELATED APPLICATION

This application claims the benefit of U.S. Provisional Patent Application Ser. No. 60/660,784, filed on Mar. 11, 2005, the entire disclosure of which is incorporated herein by reference.

FIELD OF THE INVENTION

The invention relates to a method for treating proliferative disorders, particularly cancer, by administering a combination of agents.

BACKGROUND OF THE INVENTION

Therapy for proliferative disorders such as cancer has advanced significantly. Many proliferative disorders can now be effectively treated by administering therapeutic agents that include natural products, derivatives of natural products and synthetic compounds. Therapy for proliferative disorders, particularly cancer chemotherapy, may comprise administration of a combination of agents.

I. Anthracycline Cancer Chemotherapeutic Agents

The anthracyclines are a well known class of chemotherapeutic compounds that are useful for the treatment of a range of cancers. The class also includes investigational chemotherapeutic agents that are believed likely to be useful for the treatment of cancer. The prototypical anthracyclines were polyketide natural products from *Streptomyces* species, whose structure contains an 1,2,3,4-tetrahydronaphthacene-6,11-dione moiety, with an aminoglycoside side chain attached at the 1-position, although the class now also includes synthetic analogues. Examples of the anthracyclines include: doxorubicin, aclarubicin, amrubicin, carubicin, daunorubicin, epirubicin, esorubicin, idarubicin, iododoxorubicin, mitoxantrone, pirarubicin, valrubicin, and zorubicin. Those which are currently approved by the United States Food and Drug Administration (FDA) for use in cancer treatment include: doxorubicin, daunorubicin, epirubicin, idarubicin, mitoxantrone, and valrubicin. The use of the agents, as with many chemotherapeutic agents, is limited by their toxicity. The toxic effects of anthracycline chemotherapeutic agents include myelosuppression, alopecia, diarrhea, nausea, and vomiting. One of the most serious and limiting toxic effects of anthracyclines is cardiac toxicity, which may be manifested years after treatment with the drug in symptoms such as clinical heart failure. The effect toxic is believed to cumulative, and therefore the total dose that can be given to a patient is limited. For example, for doxorubicin, the most widely used member of the class, it is believed that the maximum lifetime cumulative dose that can be safely given is about 400 to 450 mg/m$^2$.

Doxorubicin

Doxorubicin, an anthracycline antibiotic isolated from *Streptomyces peucetius* var *caesius*, is therapeutically useful in the treatment of a broad range of cancers. See South African patent 68,02378 and U.S. Pat. No. 3,590,028, the entire disclosures of which are incorporated herein by reference. The structure of doxorubicin is as shown in Scheme 1 below.

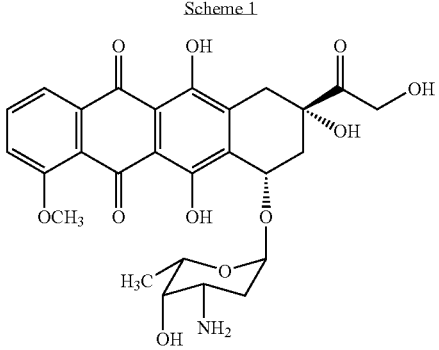

Scheme 1

Doxorubicin

Proliferative disorders for which doxorubicin is administered include acute lymphocytic (lymphoblastic) leukemia; acute non-lymphocytic (myeloblastic) leukemia; breast carcinoma; gastric carcinoma; small cell lung carcinoma; ovarian carcinoma; epithelial carcinoma; thyroid carcinoma; neuroblastoma; Wilm's tumor; transitional bladder cell carcinoma; chronic lymphocytic leukemia; cervical carcinoma; endometrial carcinoma; head and neck carcinoma; primary hepatocellular carcinoma; non-small cell lung carcinoma; pancreatic carcinoma; hepatoblastoma; thymoma; ovarian germ cell tumors; trophoblastic gestational tumors; prostate carcinoma; Hodgkin's lymphoma; non-Hodgkin's lymphoma; Ewing's sarcoma; acquired immunodeficiency syndrome (aids)-associated Kaposi's sarcoma; osteosarcoma; soft tissue sarcoma; multiple myeloma; adrenocortical carcinoma; advanced carcinoid tumors; inoperable esophageal carcinoma; and retinoblastoma.

II. Platinum-Based Cancer Chemotherapeutic Agents

The platins are a well known class of chemotherapeutic compounds (also called platinum-based chemotherapeutic compounds) that are useful for the treatment of proliferative disorders, particularly cancers. The class also includes investigational chemotherapeutic agents that are believed likely to be useful for the treatment of such proliferative diseases. Chemically, the platins are platinum (II) or platinum (IV) complexes which usually conform to the general structure cis-[PtX$_2$(Am)$_2$] or cis-[PtX$_2$Y$_2$(Am)$_2$], where X is an anionic leaving group, Am is an inert amine with at least one NH moiety, X and Am are in a square planar configuration about the platinum, cis denoting that the two X ligands are in a cis configuration relative to each other, and Y is another ligand. The two inert amines in the complex may be distinct ligands or part of single chelating diamine ligand. Similarly the two leaving groups X may be distinct ligands (e.g. chloride) or part of a single chelating ligand (e.g. oxalate). See E. Wong and C. M. Giandomenico, *Chem. Rev.*, 1999, 99, 2451-66, the entire disclosure of which is incorporated herein by reference. These general structures are depicted in Scheme 2 below. Examples of the platins include: cisplatin, carboplatin, oxaliplatin, iproplatin, lobaplatin, picoplatin, satraplatin, spiroplatin, tetraplatin, and zeniplatin. The platins which are currently approved by the FDA for use in cancer treatment include: cisplatin, carboplatin, and oxaliplatin.

The use of the platins, as with many chemotherapeutic agents, is limited by their toxicity. The toxic effects of platins include myelosuppression, peripheral neuropathy, alopecia, diarrhea, nausea, and vomiting. One of the most serious and limiting toxic effects of the platins, particularly cisplatin, is nephrotoxicity. With cisplatin, renal toxicity is observed in about 30% of patients given a 50 mg/m² dose, and the renal toxicity becomes more prolonged and severe with repeated doses of the drug.

Scheme 2

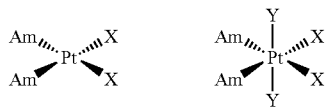

Oxaliplatin

Oxaliplatin is an alkylating agent useful in the treatment of proliferative disorders. See, U.S. Pat. Nos. 5,290,961, 5,338,874 and 5,420,319, the entire disclosures of which are incorporated herein by reference. Proliferative disorders for which oxaliplatin is administered include advanced carcinoma of the colon or rectum. Oxaliplatin antiproliferative activity has also been studied in hepatocellular carcinoma (Becouarn et al., *Crit. Rev. Oncol. Hematol.*, 2001, 40(3), 265-72; and Caussanel et al., *J. Natl. Cancer Inst.*, 1990, 82(12), 1046-50); breast cancer (Cottu et al., *Proc. Am. Soc. Clin. Oncol.*, 2000, 19, 155a); gastric cancer (Louvet et al., *Proc. Am. Soc. Clin. Oncol.*, 2000, 19, 265a); germ cell cancer (Soulie et al., *J. Cancer Res., Clin. Oncol.*, 1999, 125(12), 707-11); head and neck cancer (Degardin et al., *Eur. J. Cancer Part B, Oral Oncol.*, 1996, 32B(4), 278-79); non-small cell lung cancer (Monnet et al., *Eur. J. Cancer*, 1998, 34(7), 1124-27); non-Hodgkin's lymphoma (Germann et al., *Ann. Oncol.*, 1999, 10(3), 351-54); mesothelioma (Fizazi et al., *Proc. Am. Soc. Clin. Oncol.*, 2000, 19, 578a); ovarian cancer (Piccart et al., *J. Clin. Oncol.*, 2000, 18(6), 1193-202); pancreatic cancer (Rougier et al., *Proc. Am. Soc. Clin. Oncol.*, 2000, 19, 262a); and prostate cancer (Droz et al., *Proc. Am. Soc. Clin. Oncol.*, 2000, 19, 359a (meeting abstract 1415)). The entire disclosures of the above references are incorporated herein by reference.

The structure of oxaliplatin is shown in Scheme 3 below.

Scheme 3

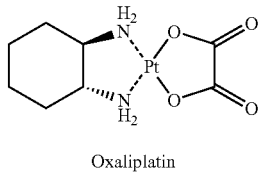

Oxaliplatin

Numerous advances have been made in the treatment of proliferative disorders such as cancer. However, new therapies are needed which are capable of treating proliferative disorders.

Because of the toxicity and side effects shown by the above-mentioned chemotherapeutic agents, the need exists for new therapies in the treatment of proliferative diseases, particularly therapies which that have greater potency, lower toxicity and/or activity across a broader spectrum of cell types. One solution would be a composition containing, or method of using the above-mentioned therapeutic agents, wherein the efficacy is improved, for example by a synergistic combination with another compound. Such compositions or methods could be very valuable in the treatment of proliferative diseases. Using such compositions or methods in the treatment of proliferative diseases could provide greater efficacy, or potency, resulting in improved therapeutic response, diminished side effects, or both, as compared to using the above-mentioned chemotherapeutic agents alone.

SUMMARY OF THE INVENTION

Accordingly, the present invention is directed to a combination of antiproliferative agents, and to a method for treating cancer or other proliferative disorders, comprising administering the antiproliferative agents in combination.

According to one embodiment of the invention, a composition is provided comprising at least one compound according to Formula I:

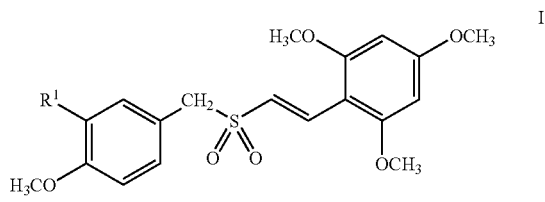

wherein $R^1$ is selected from the group consisting of —OH, —NH$_2$, —NH—CH$_2$—CO$_2$H, —NH—CH(CH$_3$)—CO$_2$H, and —NH—C(CH$_3$)$_2$—CO$_2$H, or a pharmaceutically acceptable salt of such a compound; and at least one chemotherapeutic agent selected from the group consisting of anthracyclines, platins, and pharmaceutically acceptable salts thereof.

In one embodiment of the invention, the at least one chemotherapeutic agent comprises at least one anthracycline, or a pharmaceutically acceptable salt thereof, preferably doxorubicin, aclarubicin, amrubicin, carubicin, daunorubicin, epirubicin, esorubicin, idarubicin, iododoxorubicin, mitoxantrone, pirarubicin, valrubicin, zorubicin, or a pharmaceutically acceptable salt thereof, and more preferably doxorubicin, daunorubicin, epirubicin, idarubicin, mitoxantrone, valrubicin, or a pharmaceutically acceptable salt thereof, and most preferably doxorubicin, or a salt thereof. In other embodiments of the invention, the at least one chemotherapeutic agent comprises an anthracycline, or a salt thereof, other than doxorubicin and salts thereof.

In another embodiment of the invention, the at least one therapeutic agent comprises at least one platin or a pharmaceutically acceptable salt thereof, preferably cisplatin, carboplatin, oxaliplatin, iproplatin, lobaplatin, picoplatin, satraplatin, spiroplatin, tetraplatin, zeniplatin, or a pharmaceutically acceptable salt thereof, more preferably cisplatin, carboplatin, oxaliplatin, or a pharmaceutically acceptable salt thereof, and most preferably oxaliplatin. In other embodiments of the invention, the at least one chemotherapeutic agent comprises a platin other than oxaliplatin.

In another embodiment of the invention, the compound according to Formula I is (E)-5-((2,4,6-trimethoxystyrylsulfonyl)methyl)-2-methoxyphenol or (E)-2-(5-((2,4,6-trimethoxystyrylsulfonyl)methyl)-2-methoxyphenylamino) acetic acid, or a pharmaceutically acceptable salt of such a compound.

Most preferably, the compound according to Formula I is (E)-2-(5-((2,4,6-trimethoxystyrylsulfonyl)methyl)-2-methoxyphenylamino)acetic acid sodium salt ("Compound A").

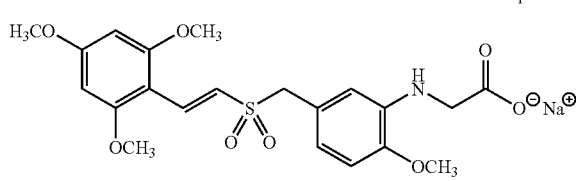

Compound A

In one embodiment, the composition of the invention comprises at least one compound according to Formula I, as defined above, or a pharmaceutically acceptable salt thereof, and, either oxaliplatin or doxorubicin, or a pharmaceutically acceptable salt thereof. Doxorubicin is preferably employed as a pharmaceutically acceptable acid addition salt.

In one embodiment, the Formula I compound is selected from the group consisting of (E)-5-((2,4,6-trimethoxystyrylsulfonyl)methyl)-2-methoxyphenol, (E)-5-((2,4,6-trimethoxystyrylsulfonyl)methyl)-2-methoxybenzenamine, (E)-2-(5-((2,4,6-trimethoxystyrylsulfonyl)methyl)-2-methoxyphenylamino)acetic acid, racemic-(E)-2-(5-((2,4,6-trimethoxystyrylsulfonyl)methyl)-2-methoxyphenylamino) propanoic acid, (E)-(R)-2-(5-((2,4,6-trimethoxystyrylsulfonyl)methyl)-2-methoxyphenylamino) propanoic acid, (E)-(S)-2-(5-((2,4,6-trimethoxystyrylsulfonyl)methyl)-2-methoxyphenylamino) propanoic acid and (E)-2-(5-((2,4,6-trimethoxystyrylsulfonyl)methyl)-2-methoxyphenylamino)-2-methylpropanoic acid, or a pharmaceutically acceptable salt of such a compound.

In another aspect of the invention, there is provided the above-described composition of the invention, including any of the embodiments thereof, for use in medicine.

In another aspect of the invention, there is provided the use of the above-described composition of the invention, including any of the embodiments thereof, in the manufacture of a medicament for the treatment of a proliferative disorder preferably cancer, and more preferably ovarian cancer, cervical cancer, breast cancer, liver cancer, prostate cancer, testicular cancer, lung cancer, renal cancer, colorectal cancer, skin cancer, brain cancer and leukemia.

In another aspect of the invention, there are provided methods of treating an individual for a proliferative disorder, preferably cancer, and more preferably ovarian cancer, cervical cancer, breast cancer, liver cancer, prostate cancer, testicular cancer, lung cancer, renal cancer, colorectal cancer, skin cancer, brain cancer and leukemia.

In one embodiment of this aspect of the invention, there are provided methods of treating an individual for a proliferative disorder, particularly cancer, comprising administering to the individual in need of such treatment, an effective amount of the composition of the invention. In particular embodiments of this aspect the invention, the composition is any one of the above-described particular embodiments of the composition of the invention.

In another embodiment of this aspect of the invention, there are provided methods of treating an individual for a proliferative disorder, particularly cancer, comprising administering to the individual in need of such treatment, an effective amount of at least one compound according to Formula I, as defined above, and an effective amount of a chemotherapeutic agent selected from the group consisting of anthracyclines, platins, and pharmaceutically acceptable salts thereof.

In particular embodiments of this aspect of the invention, the chemotherapeutic agent is an anthracycline, or a pharmaceutically acceptable salt thereof, preferably doxorubicin, aclarubicin, amrubicin, carubicin, daunorubicin, epirubicin, esorubicin, idarubicin, iododoxorubicin, mitoxantrone, pirarubicin, valrubicin, zorubicin, or a pharmaceutically acceptable salt thereof, more preferably doxorubicin, daunorubicin, epirubicin, idarubicin, mitoxantrone, valrubicin, or a pharmaceutically acceptable salt thereof.

In particular embodiments of this aspect of the invention, the chemotherapeutic agent is a platin or a pharmaceutically acceptable salt thereof, preferably cisplatin, carboplatin, oxaliplatin, iproplatin, lobaplatin, picoplatin, satraplatin, spiroplatin, tetraplatin, zeniplatin, or a pharmaceutically acceptable salt thereof, more preferably cisplatin, carboplatin, oxaliplatin, or a pharmaceutically acceptable salt thereof.

In particular embodiments of this aspect of the invention, the compound according to Formula I is (E)-5-((2,4,6-trimethoxystyrylsulfonyl)methyl)-2-methoxyphenol or (E)-2-(5-((2,4,6-trimethoxystyrylsulfonyl)methyl)-2-methoxyphenylamino)acetic acid, or a pharmaceutically acceptable salt of such a compound, preferably (E)-2-(5-((2,4,6-trimethoxystyrylsulfonyl)methyl)-2-methoxyphenylamino)acetic acid sodium salt.

In preferred embodiments of this aspect of the invention, the chemotherapeutic agent is either oxaliplatin, or doxorubicin, or a pharmaceutically acceptable salt thereof. Doxorubicin is preferably employed as a pharmaceutically acceptable acid addition salt. The compound according to Formula I is preferably (E)-5-((2,4,6-trimethoxystyrylsulfonyl)methyl)-2-methoxyphenol or (E)-2-(5-((2,4,6-trimethoxystyrylsulfonyl)-methyl)-2-methoxyphenylamino)acetic acid, or a pharmaceutically acceptable salt thereof, most preferably (E)-2-(5-((2,4,6-trimethoxystyrylsulfonyl)methyl)-2-methoxyphenylamino)acetic acid sodium salt.

In another aspect of the invention, there is provided a kit comprising, in a first compartment, a compound according to Formula I, as defined above, or a pharmaceutically acceptable salt thereof; and, in a second compartment, a chemotherapeutic agent selected from the group consisting of anthracyclines, platins, and pharmaceutically acceptable salts thereof.

In particular embodiments of this aspect of the invention, the chemotherapeutic agent is an anthracycline, or a pharmaceutically acceptable salt thereof, preferably doxorubicin, aclarubicin, amrubicin, carubicin, daunorubicin, epirubicin, esorubicin, idarubicin, iododoxorubicin, mitoxantrone, pirarubicin, valrubicin, zorubicin, or a pharmaceutically acceptable salt thereof, more preferably doxorubicin, daunorubicin, epirubicin, idarubicin, mitoxantrone, valrubicin, or a pharmaceutically acceptable salt thereof, most preferably doxorubicin, or a pharmaceutically acceptable salt thereof.

In other embodiments of this aspect of the invention, the chemotherapeutic agent is a platin or a pharmaceutically acceptable salt thereof, preferably cisplatin, carboplatin, oxaliplatin, iproplatin, lobaplatin, picoplatin, satraplatin, spiroplatin, tetraplatin, zeniplatin, or a pharmaceutically acceptable salt thereof, more preferably cisplatin, carboplatin, oxaliplatin, or a pharmaceutically acceptable salt thereof, most preferably oxaliplatin.

In other embodiments of this aspect of the invention, the compound according to Formula I is (E)-5-((2,4,6-trimethoxystyrylsulfonyl)methyl)-2-methoxyphenol or (E)-2-(5-((2,4,6-trimethoxystyrylsulfonyl)methyl)-2-methoxyphenylamino)acetic acid, or a pharmaceutically acceptable salt of such a compound, preferably (E)-2-(5-((2,4,6-trimethoxystyrylsulfonyl)methyl)-2-methoxyphenylamino)acetic acid sodium salt.

In preferred embodiments of this aspect of the invention, the chemotherapeutic agent is either oxaliplatin, or doxorubicin, or a pharmaceutically acceptable salt thereof. Doxorubicin is preferably employed as a pharmaceutically acceptable acid addition salt. The compound according to Formula I is preferably (E)-5-((2,4,6-trimethoxystyrylsulfonyl)methyl)-2-methoxyphenol or (E)-2-(5-((2,4,6-trimethoxystyrylsulfonyl)-methyl)-2-methoxyphenylamino)acetic acid, or a pharmaceutically acceptable salt thereof, most preferably (E)-2-(5-((2,4,6-trimethoxystyrylsulfonyl)methyl)-2-methoxyphenylamino)acetic acid sodium salt.

In another aspect of the invention, there is provided the use of at least one compound according to Formula I, as defined above, preferably (E)-5-((2,4,6-trimethoxystyrylsulfonyl)methyl)-2-methoxyphenol or (E)-2-(5-((2,4,6-trimethoxystyrylsulfonyl)methyl)-2-methoxyphenylamino)acetic acid, or a pharmaceutically acceptable salt thereof, most preferably (E)-2-(5-((2,4,6-trimethoxystyrylsulfonyl)methyl)-2-methoxyphenylamino)acetic acid sodium salt, in the manufacture of a medicament for administration concomitantly or sequentially with at least one chemotherapeutic agent selected from the group consisting of anthracyclines, platins, and pharmaceutically acceptable salts thereof, for the treatment of proliferative diseases.

In this aspect of the invention, the chemotherapeutic agent is an anthracycline, preferably doxorubicin, aclarubicin, amrubicin, carubicin, daunorubicin, epirubicin, esorubicin, idarubicin, iododoxorubicin, mitoxantrone, pirarubicin, valrubicin, zorubicin, or a pharmaceutically acceptable salt thereof, more preferably doxorubicin, daunorubicin, epirubicin, idarubicin, mitoxantrone, valrubicin, or a pharmaceutically acceptable salt thereof, most preferably doxorubicin, or a pharmaceutically acceptable salt thereof.

In other embodiments of this aspect of the invention, the chemotherapeutic agent is a platin or a pharmaceutically acceptable salt thereof, preferably cisplatin, carboplatin, oxaliplatin, iproplatin, lobaplatin, picoplatin, satraplatin, spiroplatin, tetraplatin, zeniplatin, or a pharmaceutically acceptable salt thereof, more preferably cisplatin, carboplatin, oxaliplatin, or a pharmaceutically acceptable salt thereof, most preferably oxaliplatin.

It is to be understood that other particular and preferred embodiments of the invention will combine the features of particular and preferred embodiments explicitly described above. Embodiments defined by such combinations are contemplated as particular embodiments of the invention.

It is to be understood that both the foregoing general description and the following detailed description are exemplary and explanatory and are intended to provide further explanation of the invention as claimed.

DEFINITIONS

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) includes human beings and non-human animals, including both mammals and non-mammals. Mammals include, for example, humans; non-human primates, e.g. apes and monkeys; cattle; horses; sheep; and goats. Non-mammals include, for example, fish and birds.

The expression "effective amount" in connection with the treatment of a patient suffering from a proliferative disorder, particularly a cancer, refers to the amount of a composition, or of each active agent, according to the invention that inhibits the growth of cells that are proliferating at an abnormally high rate or alternatively induces apoptosis of such cells, preferably cancer cells, resulting in a therapeutically useful and selective cytotoxic effect on proliferative cells when administered to a patient suffering from a proliferative disorder, particularly a cancer.

The expression "proliferative disorder" means a disorder wherein cells are made by the body at an atypically accelerated rate.

Some of the compounds according to Formula I may be characterized by isomerism resulting from the presence of a chiral center. The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. *Advanced Organic Chemistry*, Jerry March, John 4$^{th}$ Edition (Wiley 1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example shown in Scheme 4 below, the Cahn-Ingold-Prelog ranking is A>B>C>D. The lowest ranking atom, D is oriented away from the viewer.

Scheme 4

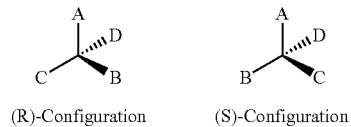

(R)-Configuration    (S)-Configuration

Unless otherwise indicated, both absolute configurations and mixtures thereof are included in the scope of compounds of Formula I which contain a chiral center.

Reference to an optically active compound according to Formula I as an (R)- or (S)-enantiomer means that the compound contains the (R)- or (S)-enantiomer and is substantially free of the other enantiomer.

The expression "substantially free" of the other enantiomer means the (R)- and (S)-enantiomers of the compound of Formula I have been separated such that the composition contains 80% or more by weight of one of the two enantiomers. Preferably, the composition contains 90% or more by weight of a single enantiomer. More preferably, the composition contains 95% or more by weight of a single enantiomer. Most preferably, the composition contains 99% or more by weight of a single enantiomer.

Thus, by an (R)-enantiomer of a compound according to Formula I is meant a compound that is substantially free of the (S)-enantiomer and that the compound thereby comprises 80% or more by weight of its (R)-enantiomer and likewise contains 20% or less of its (S)-enantiomer as a contaminant, by weight.

Isolated optical isomers may be purified from racemic mixtures by well-known chiral separation techniques. According to one such method, a racemic mixture of a compound having the structure of Formula I, or a chiral intermediate thereof, is separated into 99% pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Nomenclature employed herein for providing systematic names for compounds disclosed herein may be derived using the computer program package, CHEMDRAW®, CambridgeSoft Corporation, Cambridge, Mass. 02140.

DETAILED DESCRIPTION OF THE INVENTION

I. Treatment of Proliferative Disorders

Figure 1A:
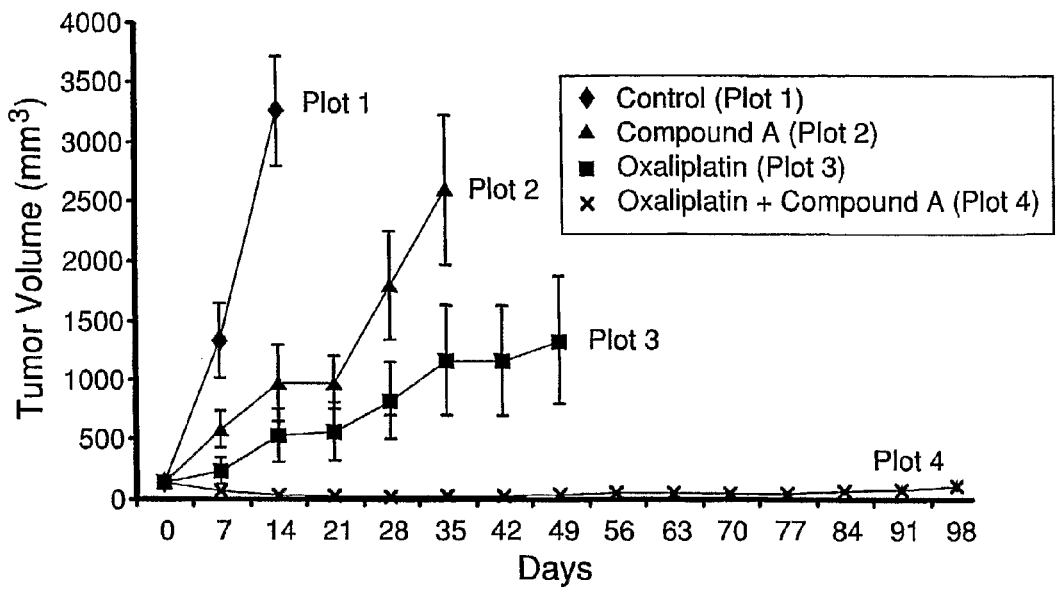
FIG. 1(a) is a graph of the effect of the intraperitoneal administration of (i) (E)-2-(5-((2,4,6-trimethoxystyrylsulfonyl)methyl)-2-methoxyphenylamino)acetic acid sodium salt (Compound A) (200 mg/kg) (▲), (ii) oxaliplatin (5 mg/kg) (■), (iii) a combination of Compound A (200 mg/kg) and oxaliplatin (5 mg/kg) (✖), or (iv) phosphate-buffered saline (PBS) vehicle (♦), on in vivo growth of BEL-7402 tumor cells (human hepatoma cell line) in nude mice following subcutaneous injection of $1\times10^7$ of the cells showing a plot of the mean tumor volume.

According to the present invention, compounds according to Formula I or a pharmaceutically acceptable salt thereof, and either an anthracycline, for example doxorubicin, or a pharmaceutically acceptable salt thereof, or a platin, for example oxaliplatin, or a pharmaceutically acceptable salt thereof, are administered in combination to inhibit proliferation of cancer cells, and kill various cancer cell types. It is believed that abnormally proliferative cells are killed at concentrations where normal cells may be temporarily growth-arrested but not killed, or where killing of normal cells is reduced.

A. Treatment of Cancer

The compositions and methods according to the invention may be employed in therapy to individuals (animals, including mammals, including humans) afflicted with cancer. The compositions of the invention are believed to inhibit the proliferation of abnormally proliferating cells, particularly cancer cells, and/or induce cell death.

The compositions and methods of the invention are believed effective against a broad range of cancer types, including but not limited to the following: ovarian cancer; cervical cancer; breast cancer; liver cancer, prostate cancer; testicular cancer, lung cancer, renal cancer; colorectal cancer; skin cancer; brain cancer; and leukemia, including acute myeloid leukemia, chronic myeloid leukemia, acute lymphoid leukemia, and chronic lymphoid leukemia.

More particularly, cancers that may be treated by the compositions and methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers including, for example, neuroblastoma.

The anthracyclines have demonstrated therapeutic utility in the treatment of a range of cancers. Specifically, the most widely used member of the class, doxorubicin, has demonstrated therapeutic utility in the treatment of acute lymphocytic leukemia, acute nonlymphocytic leukemia, breast carcinoma, gastric carcinoma, small cell lung carcinoma, ovarian carcinoma, epithelial carcinoma, thyroid carcinoma, neuroblastoma, Wilm's tumor, transitional bladder cell carcinoma, chronic lymphocytic leukemia, cervical carcinoma, endometrial carcinoma, head and neck carcinoma, primary hepatocellular carcinoma, non-small cell lung carcinoma, pancreatic carcinoma, hepatoblastoma; thymoma, ovarian germ cell tumors, trophoblastic gestational tumors, prostate carcinoma, Hodgkin's lymphoma, non-Hodgkin's lymphoma, Ewing's sarcoma, acquired immunodeficiency syndrome (aids)-associated Kaposi's sarcoma, osteosarcoma, soft tissue sarcoma, multiple myeloma, adrenocortical carcinoma, advanced carcinoid tumors, inoperable esophageal carcinoma, and retinoblastoma. Other anthracyclines have demonstrated utility in at least some of these diseases. For example, daunorubicin has been used in the treatment of: acute lymphocytic leukemia, acute non-lymphocytic leukaemia, acute myeloid leukemia, Ewing's sarcoma, chronic myelogenous leukemia, Hodgkin's and non-Hodgkin's lymphoma, Kaposi's sarcoma, lymphosarcoma, rhabdomyosarcoma, and Wilm's tumor; epirubicin has been used in the treatment of: breast cancer, gastric cancer, small cell and non-small cell lung cancer, Hodgkin's and non-Hodgkin's lymphoma, and ovarian cancer, bladder cancer, and soft tissue sarcoma, including pediatric soft tissue sarcoma; idarubicin has been used in the treatment of breast cancer, acute lymphocytic leukemia, acute non-lymphocytic leukemia, non-Hodgkin's lymphoma and acute and chronic myelogenous leukemia; mitoxantrone has been used in the treatment of: acute myelogenous leukemia, acute non-lymphocytic leukemia, breast cancer, Non-Hodgkin's lymphoma, acute lymphocytic leukemia, chronic myelogenous leukemia, gastric cancer, liver cancer, ovarian cancer, and prostate cancer; and valrubicin has been used in the treatment of bladder cancer. Accordingly, administration of compositions according to the invention wherein the chemotherapeutic agent is an anthracycline, particularly doxorubicin or a pharmaceutically acceptable salt thereof, are particularly useful in the treatment of these proliferative disorders.

Compositions and methods according to the present invention wherein the compound according to Formula I is (E)-2-(5-((2,4,6-trimethoxystyrylsulfonyl)methyl)-2-methoxyphenylamino)acetic acid, or a pharmaceutically acceptable salt thereof, and the chemotherapeutic agent is doxorubicin, or a pharmaceutically acceptable salt thereof are particularly preferred for treatment of breast cancer, more particularly, estrogen dependent breast cancer.

The platins likewise have demonstrated therapeutic utility in the treatment of a range of cancers. The most widely used, cisplatin, has been used for an extremely broad range of indications. Examples of such indications include: bladder cancer, brain cancer, cervical cancer, esophageal cancer, gastric cancer, germ cell tumors, gestational trophoblastic neoplasia, head and neck cancer, small cell and non-small cell lung cancer, Hodgkin's and non-Hodgkin's lymphoma, mesothelioma, nasopharyngeal cancer, neuroblastoma, osteosarcoma, ovarian cancer, prostate cancer, testicular cancer, Wilm's tumor, adrenal carcinoma, anal cancer, breast cancer, choriocarcinoma, endometrial cancer, gastrointestinal cancer, hepatoblastoma, kidney cancer, liver cancer, lymphomas, melanoma, penile cancer, sarcoma, and thyroid cancer. Carboplatin has been used in the treatment of ovarian cancer, bladder cancer, brain tumors, breast cancer, cervical cancer, endometrial cancer, Ewing's sarcoma, germ cell tumors, head and neck cancer, acute lymphocytic leukaemia, non-Hodgkin's lymphoma, melanoma, neuroblastoma, osteosarcoma, small cell and non-small cell lung cancer, retinoblastoma, rhabdomyosarcoma, testicular cancer and Wilm's tumor. Oxaliplatin has demonstrated therapeutic utility in the treatment of advanced carcinoma of the colon or rectum, breast cancer, gastric cancer, germ cell cancer, head and neck cancer, non-small cell lung cancer, non-Hodgkin's lymphoma, mesothelioma, ovarian cancer, pancreatic cancer, and prostate cancer. Accordingly, administration of compositions according to the invention wherein the chemotherapeutic agent is a platin, particularly oxaliplatin, or a pharmaceutically acceptable salt thereof, are particularly useful in the treatment of these proliferative disorders.

Compositions and methods according to the present invention wherein the compound according to Formula I is (E)-2-(5-((2,4,6-trimethoxystyrylsulfonyl)methyl)-2-methoxyphenylamino)acetic acid, or a pharmaceutically acceptable salt thereof, and the chemotherapeutic agent is oxaliplatin, or a pharmaceutically acceptable salt thereof are particularly preferred for treatment of hepatoma. Such compositions are also particularly preferred for the treatment of prostate cancer.

Cancers treated according to the present invention may be solid tumors that may or may not be metastatic. Cancers may also occur, as in leukemia, as a diffuse tissue.

B. Treatment of Non-Cancer Proliferative Disorders

The compositions and methods of the invention are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Non-cancer proliferative disorders believed treatable by compositions and methods of the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's Disease of the bone, fibrocystic disease of the breast, uterine fibroids, Peyronies and Dupuytren's fibrosis, restenosis, benign proliferative breast disease, benign prostatic hyperplasia, X-linked lymphoproliferative disorder (Duncan disease), post-transplantation lymphoproliferative disorder (PTLD), macular degeneration, and retinopathies, such as diabetic retinopathies and proliferative vitreoretinopathy (PVR).

Other non-cancer proliferative disorders believed treatable by compositions and methods of the invention include the presence of pre-cancerous lymphoproliferative cells associated with an elevated risk of progression to a cancerous disorder. Many non-cancerous lymphoproliferative disorders are associated with latent viral infections such as Epstein-Barr virus (EBV) and Hepatitis C. These disorders often begin as a benign pathology and progress into lymphoid neoplasia as a function of time.

II. The Advantages of the Invention

We have discovered that when a compound of Formula I is combined with an anthracycline or a platin chemotherapeutic agent in xenograft models of cancer treatment where mice are injected with human tumor cell lines and treated with the compounds, a surprising advantage is seen from using a combination of the compounds as compared to using the compounds separately. The experiments are described in detail in Examples 6 to 9 below.

In the experiment of Example 6, mice implanted with BEL-7402 tumor cells (human hepatoma cell line) were treated every other day by intraperitoneal injection of (E)-2-(5-((2,4,6-trimethoxystyrylsulfonyl)methyl)-2-methoxyphenylamino)acetic acid sodium salt (200 mg/kg), oxaliplatin (5 mg/kg), or a combination of (E)-2-(5-((2,4,6-trimethoxystyrylsulfonyl)methyl)-2-methoxyphenylamino)acetic acid sodium salt (200 mg/kg) and oxaliplatin (5 mg/kg). FIG. 1($a$) shows the average tumor volumes as a function of time after commencement of treatment. Although (E)-2-(5-((2,4,6-trimethoxystyrylsulfonyl)methyl)-2-methoxyphenylamino)acetic acid sodium salt alone or oxaliplatin alone both slowed the growth of the tumor, but the tumors nevertheless continued to grow. A much more dramatic reduction in the rate of tumor growth was observed in the animals treated with the combination of oxaliplatin and (E)-2-(5-((2,4,6-trimethoxystyrylsulfonyl)methyl)-2-methoxyphenylamino)acetic acid sodium salt. A synergistic effect was observed resulting in complete disappearance of the tumor mass for animals in the dosing group receiving the combination therapy. In addition, there was no evidence of toxicity of the combination as assessed by the body weight data shown in FIG. 1($b$), where the combination-treated animals did not show significant weight loss even after 100 days treatment.

Figure 2:
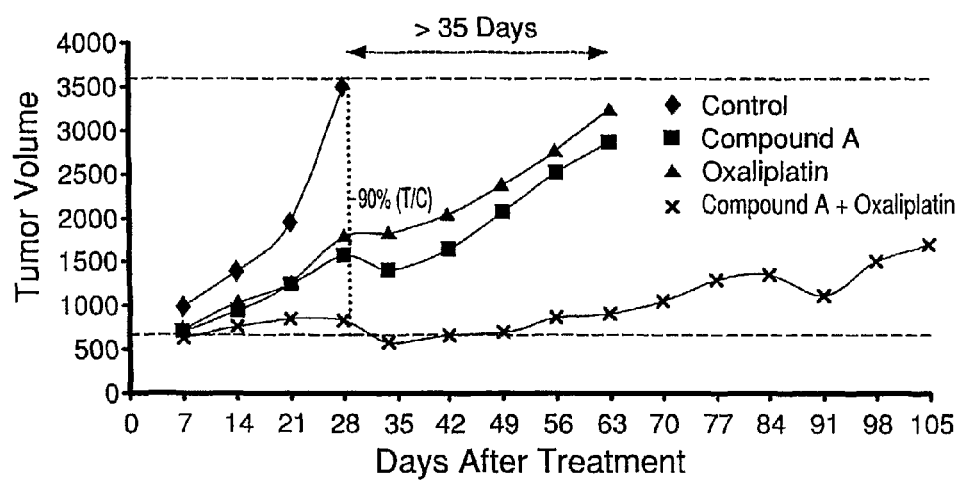
FIG. 2 is a graph of the effect of the intraperitoneal administration of (i) Compound A (200 mg/kg) (■), (ii) oxaliplatin (5 mg/kg) (▲), (iii) a combination of Compound A (200 mg/kg) and oxaliplatin (5 mg/kg) (✖), or (iv) PBS vehicle (♦), on in vivo growth of DU145 tumor cells (human prostate cancer cell line) in nude mice following subcutaneous injection of $1\times10^7$ of the cells, showing the mean tumor volume.

A similar synergistic effect was seen in the experiment of Example 7, where mice implanted with DU145 tumor cells (human prostate cancer cell line) were treated every other day by intraperitoneal injection of (E)-2-(5-((2,4,6-trimethoxystyrylsulfonyl)methyl)-2-methoxyphenylamino)acetic acid sodium salt (200 mg/kg), oxaliplatin (5 mg/kg), or a combination of (E)-2-(5-((2,4,6-trimethoxystyrylsulfonyl)methyl)-2-methoxyphenylamino)acetic acid sodium salt (200 mg/kg) and oxaliplatin (5 mg/kg). FIG. 2 shows the average tumor volumes as a function of time after commencement of treatment. The animals treated with single agents, either (E)-2-(5-((2,4,6-trimethoxystyrylsulfonyl)methyl)-2-methoxyphenylamino)acetic acid sodium salt or oxaliplatin, both had a significant therapeutic response and a tumor growth delay. However, growth of the tumors still proceeded, and after 63 days the tumors were of a comparable volume to those observed in control animals after 28 days. Surprisingly, however, the combination resulted in a dramatic synergistic reduction in tumor growth. The average tumor volume was reduced to below the starting volume after 28 days of treatment and the tumors failed to reach the maximum tumor volumes observed in the control mice or the mice treated with a single agent, even after 105 days. The time of tumor volume doubling was about 75 days for the mice treated with the combination therapy, in contrast to about 9 days for the control group, and 25 days for the single agent-treated groups.

Surprising synergistic effects were observed with doxorubicin as well as with oxaliplatin. In the experiment of Example 8, female mice implanted interscapularly with estradiol, which were also implanted with MCF-7 tumor cells (human breast cancer cell line) were treated every other day by intraperitoneal injection of either (E)-2-(5-((2,4,6-trimethoxystyrylsulfonyl)methyl)-2-methoxyphenylamino) acetic acid sodium salt (200 mg/kg) alone, doxorubicin (2.5 mg/kg) alone, or a combination of (E)-2-(5-((2,4,6-trimethoxystyrylsulfonyl)methyl)-2-methoxyphenylamino) acetic acid sodium salt (200 mg/kg) and doxorubicin (2.5 mg/kg). FIG. 3($a$) shows the average tumor volumes as a function of time after commencement of treatment. Both (E)-2-(5-((2,4,6-trimethoxystyrylsulfonyl)methyl)-2-methoxyphenylamino)acetic acid sodium salt (200 mg/kg) alone and doxorubicin (2.5 mg/kg) alone significantly slowed the growth of the tumors. By the $35^{th}$ day, however, all the doxorubicin-treated animals had died, despite the fact their tumors were only 500 mm$^3$, whereas all the animals treated with (E)-2-(5-((2,4,6-trimethoxystyrylsulfonyl)methyl)-2-methoxyphenylamino)acetic acid sodium salt (200 mg/kg) alone survived to 84 days. The impact of treatment with the combination of doxorubicin and (E)-2-(5-((2,4,6-trimethoxystyrylsulfonyl)methyl)-2-methoxyphenylamino)acetic acid sodium salt on tumor growth was, surprisingly, substantially greater than that of either agent separately. A synergistic effect of the combination treatment was observed, the combination resulting in complete disappearance of the tumor mass for animals in the dosing group receiving the combination therapy, and the animals lived 49 days, indicating that animals had been protected from the toxicity of doxorubicin while experiencing major improvement in therapy. In addition, as assessed by the body weight data shown in FIG. 3($b$), there was no evidence of toxicity in the combination-treated group.

The surprising protective effect of (E)-2-(5-((2,4,6-trimethoxystyrylsulfonyl)methyl)-2-methoxyphenylamino) acetic acid sodium salt upon doxorubicin treatment is also illustrated in the experiment described in Example 9. As in the experiment of Example 8, female mice implanted interscapularly with estradiol, and also implanted with MCF-7 tumor cells (human breast cancer cell line). The mice were then treated every other day by intraperitoneal injection with either doxorubicin (1 mg/kg) alone, or a combination of (E)-2-(5-((2,4,6-trimethoxystyrylsulfonyl)methyl)-2-methoxyphenylamino)acetic acid sodium salt (200 mg/kg) and doxorubicin (1 mg/kg). FIGS. 4($a$) and 4($b$) show plots of the body weights of the individual animals in each treatment group. As shown in FIG. 4($a$), animals of the group which received doxorubicin alone showed initial suggestive weight gain, but a high proportion of the animals died. Major weight loss immediately preceding death occurred in 4 of the 5 animals (as indicated in FIG. 4($a$) by the symbol ⚥). Surprisingly, and in stark contrast, in the treatment group which received the same dose of doxorubicin together with (E)-2-(5-((2,4,6-trimethoxystyrylsulfonyl)methyl)-2-methoxyphenylamino) acetic acid sodium salt, every one of the animals survived for 56 days, and every animal moderately gained weight. Thus, in this experiment, (E)-2-(5-((2,4,6-trimethoxystyrylsulfonyl) methyl)-2-methoxyphenylamino)acetic acid sodium salt showed a remarkable protective effect in a model of doxorubicin chemotherapy, increasing the survival rate from 20 to 100% for the animals of the experiment.

In light of the surprising results observed in the above-described experiments, a beneficial synergistic effect is expected when an athracycline or a platin is used in combination with a compound of Formula I for cancer chemotherapy. Because similar beneficial effects were observed in the three xenograft models of human tumors, it is believed that the combination and methods of the invention are applicable to the treatment of a broad range of proliferative diseases, particularly cancers, most particularly in humans. In addition, there is close structural similarity among the anthracycline class of anticancer agents, which contain an aminoglycoside side chain attached to the 1-position of a 1,2,3,4-tetrahydronaphthacene-6,11-dione moiety. Although the invention is not limited by theory, it is believed that because of this close structural relationship, the same combination of molecular mechanisms are likely involved in anticancer activity among members of the anthracycline class of anticancer agents, and, accordingly, the surprising effect observed with doxorubicin will also be observed when compounds of Formula I are employed in chemotherapy in combination other members of the anthracycline class. There is also close structural similarity among the platin class of anticancer agents, which comprise platinum complexes with two amine-containing groups and two leaving groups with a cis configuration as described above. Although the invention is not limited by theory, it is believed that because of the close structural similarity, that the similar molecular mechanisms are likely involved in anticancer activity among members within the platin class of anticancer agents. Specifically, the molecular mechanism within the platin class is believed to involve a common mechanism wherein the platinum complex is intercalated into DNA leading to cell cycle arrest and selective apoptosis of cancer cells. It is therefore believed that the surprising effect observed with oxaliplatin will also be observed when compounds of Formula I are employed in chemotherapy in combination other members of the platin class. Finally, Formula I above defines a limited number of structurally very similar compounds. It is believed that other compounds of Formula I will show similar effects, exerted through similar molecular mechanisms, as those observed for the representative compound of Formula I, (E)-2-(5-((2,4,6-trimethoxystyrylsulfonyl)methyl)-2-methoxyphenylamino) acetic acid sodium salt. It is therefore expected that the surprising effect observed with (E)-2-(5-((2,4,6-trimethoxystyrylsulfonyl)methyl)-2-methoxyphenylamino) acetic acid sodium salt will also be observed when other compounds of Formula I are employed in chemotherapy in combination anthracyclines or platins.

III. Preparation of Compounds According to Formula I (E)-α,β-unsaturated sulfones according to Formula I, may be prepared, for example, by Knoevenagel condensation of 2,4,6-trimethoxybenzaldehyde [830-79-5] (Aldrich Chemical, catalog # 13,871-1) with a suitably substituted 2-(benzylsulfonyl)acetic acid C (Scheme 5).

The procedure is described for synthesis of styryl sulfones by Reddy et al., *Acta. Chim. Hung.,* 1984, 115, 269-71; Reddy et al., *Sulfur Lett.,* 1991, 13, 83-90; Reddy et al., *Synthesis,* 1984, (4), 322-23; and Reddy et al., *Sulfur Lett.,* 1987, 7, 43-48, and PCT Patent Application Publications WO03/072062 and WO05/089269, the entire disclosures of which are incorporated herein by reference. A general synthesis according to a Knoevenagel condensation is depicted in Scheme 5 below.

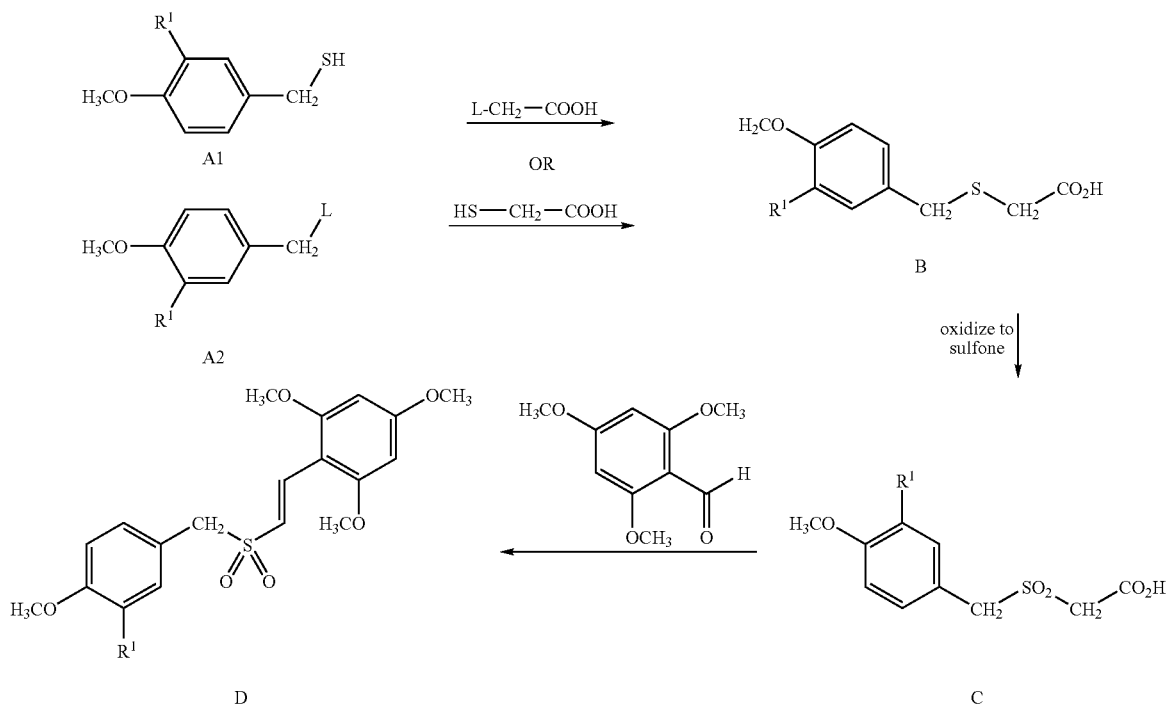

Scheme 5

The intermediate benzylsulfonyl acetic acid C, employed in Scheme 5, may be prepared by oxidation of the corresponding benzylmercaptoacetic acids B. The benzyl mercaptoacetic acid B may be prepared by reacting mercaptoacetic acid [68-11-1] (Aldrich Chemical catalog # 47,534-3) with compound A2 having a leaving group L, or by reacting an intermediate L-$CH_2$—$CO_2H$, e.g., a haloacetic acid with mercaptan A1.

In the reactions described herein for preparing compounds of Formula I, including the reactions depicted in Scheme 5, any $R^1$ groups present, and which may be reactive under the conditions of a particular reaction, may be protected during that reaction by protecting groups. Thus, preparation of compounds according to Formula I via the synthesis shown in Scheme 5 may in some instances include additional synthetic steps to add or remove a protecting group. Accordingly, for purposes of the synthesis in Scheme 5, the designation $R^1$ includes the functional groups previously listed: —OH, —$NH_2$, —NH—$CH_2$—$CO_2H$, —NH—$CH(CH_3)$—$CO_2H$, and —NH—$C(CH_3)_2$—$CO_2H$, and also includes those functional groups protected by protecting groups.

A "protecting group" is a chemical functionality which selectively blocks one or more reactive sites in a multifunctional compound such that a chemical reaction can be carried out selectively at another unprotected reactive site. Certain processes for preparation of compounds according to the present invention may rely upon protecting groups to block reactive functional groups that are present in the reactants. Examples of reactive groups which may be blocked by suitable protecting groups include —$NH_2$ or —OH groups which may be present. For example, for the preparation of a compound according to Formula I wherein $R^1$ is —OH, $R^1$ may be protected by derivatizing the —OH group as, for example, an ether, e.g., a benzyl or substituted benzyl ether. If such $R^1$ groups that are reactive under the conditions of a reaction step are not blocked by suitable protecting groups prior to reaction, unwanted side reactions may occur. For example, in a preparation according to Scheme 5, an —$NH_2$ or —OH group on the Formula A1 intermediate may react with the L-$CH_2$—$CO_2H$ intermediate in addition to, and in competition with the —SH group on the Formula A1 intermediate.

A protecting group may be introduced prior to carrying out a particular reaction that may affect a chemical group other than one that is desired. The protecting group is optionally removed at any suitable point in the synthesis after the reaction which necessitated use of the protecting group.

Protecting groups may be selected from any protecting groups described in the literature or known to the skilled chemist as suitable for the protection of the functional group which must be protected. Protecting groups may be introduced and removed by any suitable chemical synthesis method that is described in the art or known to the skilled chemist as suitable for the removal of the particular protecting group. Methods of removing protecting groups are preferably selected so as to effect selective removal of the protecting group with minimum effect on other chemical functionality in the molecule.

Protecting groups for $R^1$ that is —OH, include, for example, acetates, haloalkyl carbonates, benzyl ethers, alkylsilyl ethers, heterocyclyl ethers, and methyl or alkyl ethers. Protecting groups for $R^1$ that contains a carboxyl group include, for example, tert-butyl, benzyl or methyl esters. Protecting groups for $R^1$ that is —$NH_2$ include benzyl, 2,4-dimethoxybenzyl, CBZ, p-methoxybenzyloxycarbonyl, p-nitrobenzyloxycarbonyl, t-BOC, trifluoroacetyl. Methods for removal of hydroxy and amino protecting groups include, for example, acid, base, metal or enzyme-catalyzed hydrolysis for CBZ; acid or iodotrimethylsilane for removal of t-BOC groups; hydrogenation for benzyl and CBZ; and photolysis for o-nitrobenzyloxycarbonyl.

Protecting groups may also include different oxidation states of a chemical group. An example of such a protecting group is an aromatic nitro group in place of $R^1$, which may readily be reduced to an —$NH_2$ group.

Further examples of protecting groups can be found in *Protecting Groups in Organic Synthesis*, by Theodora W. Green and Peter G. M. Wuts, 3$^{rd}$ edition, published by Wiley & Sons, New York (1999) and *Compendium of Synthetic Organic Methods*, Harrison et al, Vols. 1-8, published by Wiley & Sons 1971-1996, the entire disclosures of which are incorporated herein by reference.

IV. Administration of Therapy According to Methods of the Invention

Antiproliferative therapy administered according to the invention is achieved by administering a combination of at least one Formula I compound, or pharmaceutically acceptable salt of such a compound, and at least one anthracycline or platin cancer chemotherapeutic agent, or a pharmaceutically acceptable salt thereof. The combination of at least Formula I compound or pharmaceutically acceptable salt of such a compound, and at least one anthracycline or platin cancer chemotherapeutic agent or a pharmaceutically acceptable salt thereof, may further comprise, or be used in combination with, other drugs, for example other anti-proliferative compounds, or drugs to control side-effects, for example antiemetic agents.

In one embodiment of the invention, the combination of at least Formula I compound or pharmaceutically acceptable salt of such a compound, and at least one anthracycline or platin chemotherapeutic agent, or a pharmaceutically acceptable salt thereof, are co-formulated and used as part of a single pharmaceutical composition or dosage form. The compositions according to this embodiment of the invention comprise at least Formula I compound or pharmaceutically acceptable salt of such a compound, and at least one anthracycline or platin chemotherapeutic agent, or a pharmaceutically acceptable salt thereof, in combination with a pharmaceutically acceptable carrier. In such compositions, the Formula I compound, or pharmaceutically acceptable salt thereof, and the anthracycline or platin chemotherapeutic agent, or pharmaceutically acceptable salt thereof, may together comprise from 0.1 to 99.99 weight percent of the total composition. The compositions may be administered by any route and according to any schedule which is sufficient to bring about the desired antiproliferative effect in the patient.

Alternatively, according to other embodiments of the invention, the combination of at least Formula I compound or pharmaceutically acceptable salt of such a compound, and at least one anthracycline or platin chemotherapeutic agent, or a pharmaceutically acceptable salt thereof, may be formulated and administered as two or more separate compositions, at least one of which comprises at least one Formula I compound, or a pharmaceutically acceptable salt of such a compound, and at least one of which comprises at least one anthracycline or platin chemotherapeutic agent, or a pharmaceutically acceptable salt thereof. The separate compositions may be administered by the same or different routes, administered at the same time or different times, and administered according to the same schedule or on different schedules, provided the dosing regimen is sufficient to bring about the desired antiproliferative effect in the patient. When the drugs are administered in serial fashion, it may prove practical to intercalate administration of the two drugs, wherein a time interval, for example a 0.1 to 48 hour period, separates administration of the two drugs.

When the Formula I compound and anthracycline or platin chemotherapeutic agent are to be administered as separate drugs according to the methods of the invention, they may each may be administered in the form of a pharmaceutical composition, comprising the active agent (i.e. either the Formula I compound or the anthracycline or platin chemotherapeutic agent) in combination with a pharmaceutically acceptable carrier. The active agent in such formulations may comprise from 0.1 to 99.99 weight percent.

Routes of administration include enteral, such as oral; and parenteral, such as intravenous, intra-arterial, intramuscular, intranasal, rectal, intraperitoneal, subcutaneous and topical routes. Preferably, compositions according to the invention are administered parenterally, more preferably intravenously.

It may be appreciated that by "administered" is meant the act of making a drug available to the patient such that a physiological effect is realized. Thus, contemplated within the scope of the present invention is the instillation of the Formula I compound or the chemotherapeutic agent (anthracycline or platin) or both in the body of the patient in a controlled or delayed release formulation, with systemic or local release of the active agents occurring at a later time and/or over a prolonged time interval. Thus, a depot of a first agent may be administered to the patient and the therapy component comprising the other agent may be administered prior to, subsequent to, or during the systemic release of the first agent.

By "pharmaceutically acceptable carrier" is meant any carrier, diluent or excipient which is compatible with the other ingredients of the formulation and not deleterious to the recipient. The active agents, whether as separate compositions or a combined composition, may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agents may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agents. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agents may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

For the administration of anthracyclines the preferred mode of administration is by intravenous injection. The compound is preferably formulated in an aqueous solution, for example, saline solution. The compound is preferably formulated as a salt, for example the hydrochloride salt. When the anthracycline is doxorubicin, the preferred formulation is a saline solution of doxorubicin as the hydrochloride salt which is preferably administered intravenously.

For the formulation of platins, the carrier of the formulation must not contain ligands that will displace the ligands of the platin, since such a formulation would be incompatible with the platin. For this reason, platins are never formulated using saline solution. The preferred formulation of platins is as a solution in aqueous dextrose, for example 5% aqueous dextrose, and the compound is preferably administered intravenously. When the platin is oxaliplatin, the preferred formulation is a solution of oxaliplatin in 5% aqueous dextrose, which is preferably administered intravenously.

The specific doses of the two active agents employed in the composition and methods of the invention to obtain the antiproliferative benefit will, of course, be determined by the particular circumstances of the individual patient. Such circumstances include the size, weight, age and sex of the patient, the nature and stage of the disease, the aggressiveness of the disease, and the route of administration.

For the anthracycline or platin chemotherapeutic agent a starting point for the determination of a suitable dose is the dose at which the anthracycline or platin has been found to be safe and effective either alone or in combination with other chemotherapeutic agents. For marketed drugs, suitable doses and dosing protocols are recommended by the manufacturer and published, for example in the Physician's Desk Reference, $58^{th}$ Edition (Thomson Healthcare, 2004), or $60^{th}$ Edition (Thomson Healthcare, 2006). For both marketed drugs and investigational chemotherapeutic agents, suitable doses are recommended and published in the literature, in reports of clinical trials of the compounds. The person skilled in the art will refer to such sources in determining a suitable dose and dosing protocol for any particular indication. Such established protocols are preferred, particularly when the anthracycline or platin chemotherapeutic agent is being administered in a separate composition from the compound of Formula I. Thus, in a preferred embodiment, the dosage, formulation, route and schedule of administration of the oxaliplatin or doxorubicin is carried out according to the known protocols for the drug.

The dose selected will depend on the particular compound being used and the route and frequency of administration. In general, suitable doses for human administration range from about 5 to about 400 mg/m$^2$, for example, about 50, 100, 200, or 300 mg/m$^2$, preferably about 10 to 100 Mg/m$^2$, for example about 10, 20, 30, 50, 60, 85, or 100 mg/m$^2$. Typically, treatment may be given weekly, or every two, three, or four weeks, with individual treatments comprising an infusion or one or more bolus doses, for example up to about three daily bolus doses. For doxorubicin, for example, numerous dosing schedules have been established, depending on the disease, response, and concomitant therapy. Examples include a weekly i.v. bolus dose of about 10 to about 20 mg/m$^2$, a three to four weekly i.v. bolus dose of about 60 to about 75 mg/m$^2$, or a four-weekly dosing regimen where an i.v. bolus dose of about 20 to about 30 mg/m$^2$ i.v. bolus dose is given daily on three sequential days. For oxaliplatin, in a typical dosing regimen, about 85 mg/m$^2$ is given by i.v. infusion every two weeks.

When anthracycline or platin chemotherapeutic agents are used in combination with compounds of Formula I in the compositions and methods of the invention, it is envisaged that the dose of the anthracycline or platin chemotherapeutic agent used may be comparable to those which have been found safe and effective the compound alone or in other combinations with other agents. However, it is envisaged that, because of the surprising synergistic effects seen when anthracyclines or platins are used in combination with compounds that lower or higher doses may be used. The ability to use lower doses of the anthracycline or platin chemotherapeutic agent in the combination is envisaged due to the surprising greater efficacy observed in the combination as compared to when the anthracycline or platin chemotherapeutic agent is used alone; the anthracycline or platin chemotherapeutic agent may therefore be effective when used in the combination at a lower dose than that at which it is effective when used alone. The ability to use higher doses of the anthracycline or platin chemotherapeutic agent in the combination is envisaged due to surprising protective effect of the compound of Formula I in preventing or lowering the toxicity of the chemotherapeutic agent.

For the compound according to Formula I, the preferred daily dose is in the range of about 1 to about 10000 mg/m$^2$, more preferably from about 5 to about 5000 mg/m$^2$, still more preferably about 10 to about 3000 mg/m$^2$, most preferably about 50 to about 1000 mg/m$^2$, for example 100, 350, 500, or 750 mg/m$^2$. Because the compounds of Formula I are believed to be of much lower toxicity than the anthracycline or platin chemotherapeutic agents, in any embodiment of the intention, the preferred sub-embodiments of the invention are those wherein the dose of the compound of Formula I exceeds that of the anthracycline or platin chemotherapeutic agent. The daily dose of the compound of Formula I may be given in a single dose, or may be divided, for example into two, three, or four doses, equal or unequal, but preferably equal, that comprise the daily dose. Such doses may be given as a bolus dose injected over, for example, about 1 to about 4 hours. Alternatively, the dose may be given by continuous intravenous infusion during the dosing period. The optimum dose and administration schedule for the compound of Formula I will depend on the dose and administration schedule of the chemotherapeutic agent. It is believed that for optimum advantage that the compound of Formula I is administered at a frequency at least equal to that at which the anthracycline or platin chemotherapeutic agent is administered. However, it may also be advantageous to continue administering the compound of Formula I between doses of the anthracycline or platin chemotherapeutic agent, or to begin administration of the compound of Formula I before and/or continue administering the compound of Formula I after the administration of the doses of the anthracycline or platin chemotherapeutic compound, for example by administering the Formula I for one day before and/or one day after weekly, two-weekly, three-weekly or four weekly administrations of the anthracycline or platin chemotherapeutic compound.

V. Salts of Compounds Utilized in the Practice of the Invention

The active agents, namely, the compounds of Formula I, anthracyclines and platins, may, where the structure of the active agent permits, take the form of salts. The term "salts" embraces salts commonly used to form alkali metal salts and to form addition salts of free acids or free bases. The term "pharmaceutically-acceptable salt" refers to salts which possess toxicity profiles within a range so as to have utility in pharmaceutical applications.

Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, alginic, B-hydroxybutyric, salicylic, galactaric and galacturonic acid.

Suitable pharmaceutically acceptable base addition salts of compounds useful in the compositions of the invention include for example, metallic salts made from calcium, magnesium, potassium, sodium and zinc or organic salts made from N,N-dibenzylethylenediamine, chloroprocaine, choline, diethanolamine, ethylenediamine, meglumine (N-methylglucamine) and procaine. For the compounds of Formula I containing a carboxyl group, alkali metal or alkaline earth metal salts are preferred. More preferred are alkali metal salts, particularly sodium salts. Preferred base addition salts of compounds according to Formula I include sodium salts of (E)-2-(5-((2,4,6-trimethoxystyrylsulfonyl)methyl)-2-methoxyphenylamino)acetic acid, racemic-(E)-2-(5-((2,4,6-trimethoxystyrylsulfonyl)methyl)-2-methoxyphenylamino)propanoic acid, (E)-(R)-2-(5-((2,4,6-trimethoxystyrylsulfonyl)methyl)-2-methoxyphenylamino)propanoic acid, (E)-(S)-2-(5-((2,4,6-trimethoxystyrylsulfonyl)methyl)-2-methoxyphenylamino)propanoic acid and (E)-2-(5-((2,4,6-trimethoxystyrylsulfonyl)methyl)-2-methoxyphenylamino)-2-methylpropanoic acid.

For base addition salts of the anthracyclines, including doxorubicin, metallic salts are preferred due to the pKa of the ionizable phenol protons in the anthracycline structure. Examples of pharmaceutically unacceptable salts include lithium salts and cyanate salts. All of these salts may be prepared by conventional means from the corresponding compound according to Formula I or anthracyclines, including doxorubicin, and platins, may be prepared by reacting, for example, the appropriate acid or base with the compound.

The practice of the invention is illustrated by the following non-limiting examples.

EXAMPLES

Example 1

Synthesis of (E)-2-(5-((2,4,6-trimethoxystyrylsulfonyl)methyl)-2-methoxyphenylamino)acetic acid A. Methyl 2-(5-((2,4,6-trimethoxystyrylsulfonyl)methyl)-2-methoxyphenylamino)acetate To a stirred solution of methyl bromoacetate (5 mmol) and sodium acetate (5 mmol) in methanol (20 mL) was added (E)-5-((2,4,6-trimethoxystyrylsulfonyl)methyl)-2-methoxybenzenamine (1 mmol). The resulting mixture was heated to reflux temperature. The heated mixture was stirred at reflux temperature for 12 to 15 h. The heated mixture was then cooled and poured onto water ice (about 100 g). A precipitate formed. The precipitate was separated by filtration to provide the product in 85% yield. m.p. 182-185° C.

B. (E)-2-(5-((2,4,6-Trimethoxystyrylsulfonyl)methyl)-2-methoxyphenylamino)acetic acid Methyl 2-(5-((2,4,6-trimethoxystyrylsulfonyl)methyl)-2-methoxyphenylamino)acetate (1 g) was dissolved in a mixture of ethanol (8 mL) and 4% aqueous sodium hydroxide (50 mL). The solution was heated to reflux temperature and maintained at reflux temperature for 10 min thereby obtaining a clear solution. The mixture was then allowed to cool to ambient temperature (25° C.), and stirred for 3 h. After 3 h, concentrated hydrochloric acid was added dropwise until a precipitate formed. The precipitate was separated by filtration, washed with water and recrystallized from 2-propanol to provide the product (E)-2,4,6-trimethoxystyryl-3-(carboxymethylamino)-4-methoxybenzylsulfone in 80% yield. m.p. 128-131° C. NMR (DMSO-d6) δ 3.76 (s, 3H), 3.80 (s, 6H), 3.82 (s, 3H), 4.23 (s, 2H), 6.25 (s, 2H), 7.06-7.09 (d, 1H vinylic), 6.66-6.74 (m, aromatic).

Example 2

Synthesis of 5-((2,4,6-trimethoxystyrylsulfonyl)methyl)-2-methoxybenzenamine

A. 4-Methoxy-3-nitrobenzylbromide

A solution of 4-methyl-2-nitroanisole (25 mmol), N-bromosuccinimide (25 mmol) and benzoyl peroxide (2.5 mmol) in carbon tetrachloride (100 mL) was heated at reflux for 18 h. The heated mixture was then poured into water. A solid precipitate formed and was separated by filtration. The aqueous filtrate was extracted with carbon tetrachloride (3×50 mL). The extract was concentrated under reduced pressure to yield a solid product. The solid products (the filtered precipitate and product of evaporating the extract) were combined and recrystallized from ethyl acetate-hexane to yield 4-methoxy-3-nitro benzyl bromide as a crystalline product in 70-75% yield. m.p. 110-112° C.

B. 4-Methoxy-3-nitrobenzylthioacetic acid

To a cold solution of sodium hydroxide (9.75 g, 240 mmol) in methanol (200 mL), was added thioglycollic acid (11.25 g, 120 mmol) slowly over 30 min. Sodium thioglycollate precipitated and was redissolved by stirring and warming the mixture. The sodium thioglycollate solution was then cooled to room temperature and 4-methoxy-3-nitrobenzyl chloride (30.0 g, 120 mmol) was added in portions to reduce the intensity of exothermic reaction. The resulting mixture was heated to reflux temperature and maintained at reflux temperature for 4 h. The heated mixture was then cooled and poured onto crushed ice (1 kg) containing hydrochloric acid (50 mL). A precipitate formed. The precipitate was separated by filtration, washed with ice cold water and dried under vacuum to yield 30 g (95% yield) of the desired 4-methoxy-3-nitrobenzylthioacetic acid product. m.p. 130-132° C.

C. 4-Methoxy-3-nitrobenzylsulfonylacetic acid

4-Methoxybenzylthioacetic acid (10 g) was dissolved in glacial acetic acid (80 mL). Hydrogen peroxide (20 mL, 30%) was added in one portion and the resulting mixture was stirred at room temperature (25° C.) for 10 h. The mixture was then poured onto crushed ice (500 g). A yellow precipitate formed. The precipitate was separated by filtration, washed with cold water and dried to provide the crude 4-methoxy-3-nitrobenzylsulfonylacetic acid product in 55% yield. Recrystallization of the crude product from hot water yielded the purified product as a crystalline solid. m.p. 96-98° C.

D. 2-((E)-2-(4-Methoxy-3-nitrobenzylsulfonyl)vinyl)-1,3,5-trimethoxybenzene

To a solution of 4-methoxy-3-nitrobenzyl sulfonylacetic acid (4.5 g, 15.5 mmol) in 30 mL of glacial acetic acid was added 2,4,6-trimethoxybenzaldehyde (3.05 g, 15.5 mmol) and a catalytic amount of benzylamine (0.6 mL). The resulting mixture was heated at reflux temperature for 6 h. The reaction mixture was then concentrated under reduced pressure to yield a gummy material. The gum was triturated with 2-propanol to yield a solid product. The solid product was recrystallized from a mixture of acetic acid and 2-propanol to provide the 2-((E)-2-(4-methoxy-3-nitrobenzylsulfonyl)vinyl)-1,3,5-trimethoxybenzene product in 28% yield. m.p. 186-187° C.

E1. (E)-5-((2,4,6-Trimethoxystyrylsulfonyl)methyl)-2-methoxybenzenamine (Reduction Method 1)

A solution of 2-((E)-2-(4-methoxy-3-nitrobenzylsulfonyl)vinyl)-1,3,5-trimethoxybenzene (1.3 mmol) in acetone-water (10:5, 25 mL) was heated to 50° C. After 30 min, sodium hydrosulfite ($Na_2S_2O_4$, 26.3 mmol) was added slowly, and the mixture was heated at reflux (50° C.) for 1 h. The heated mixture was then cooled to room temperature (25° C.) and water (25 mL) was added. A solid precipitate formed and was separated by filtration. The filtered product was washed with aqueous sodium bicarbonate. The product was distributed between water and ethyl acetate. The ethyl acetate layer was separated and dried over anhydrous sodium sulfate. The ethyl acetate was removed under reduced pressure and the crude product obtained thereby was recrystallized from 2-propanol to yield the desired (E)-5-((2,4,6-trimethoxystyrylsulfonyl)methyl)-2-methoxybenzenamine product. m.p. 148-150° C.

E2. (E)-5-((2,4,6-Trimethoxystyrylsulfonyl)methyl)-2-methoxybenzenamine (Reduction Method 2)

5% Pd/C wet (10% by weight of the nitro compound to be reduced) is charged into a flask. Pd/C was wetted with ethanol by slowly adding through the sides of the flask. 2-((E)-2-(4-Methoxy-3-nitrobenzylsulfonyl)vinyl)-1,3,5-trimethoxybenzene (10 mmol) is added to the flask and then ethanol is added sufficient to produce a 5 g/100 mL concentration of the starting nitro compound. The resulting mixture is heated to 50-60° C. Hydrazine hydrate (26 eq.) is added to the heated mixture over a period of 15-20 min. The resulting mixture is then heated at reflux temperature for 5-6 h. The progress of the reaction is monitored by thin layer chromatography (TLC). When the reaction is complete, the Pd/C is separated from the reaction mixture by filtration of the hot reaction mixture. The filtered solid is washed with hot ethanol. The volume of ethanol was reduced by 50% by distilling under reduced pressure. The reduced volume mixture is combined with an equal volume of ice cold water. The resulting mixture is stirred for 30 min. A solid precipitate forms. The precipitate is separated by filtration and dried under vacuum. The separated precipitate is recrystallized from 2-propanol to provide the (E)-5-((2,4,6-trimethoxystyrylsulfonyl)methyl)-2-methoxybenzenamine product.

Example 3

Synthesis of (E)-2-(5-((2,4,6-trimethoxystyrylsulfonyl)methyl)-2-methoxyphenylamino)propanoic acid

A. Methyl(E)-2-(5-((2,4,6-trimethoxystyrylsulfonyl)methyl)-2-methoxyphenylamino)propanoate Sodium acetate (0.4 mol) was dissolved in methanol (200 mL). Methyl-2-bromopropionate (40 mmol) was added and the resulting mixture was heated at reflux for 10 min. The heated mixture was cooled to room temperature (25° C.), and (E)-5-((2,4,6-trimethoxystyrylsulfonyl)methyl)-2-methoxybenzenamine (0.1 mol) was added. The resulting mixture was heated at reflux for 1 h. The hot reaction mixture was allowed to cool to room temperature (25° C.), and then poured into ice water (500 mL). A solid precipitate formed. The precipitate was separated by filtration and recrystallized from ethanol to provide the desired methyl(E)-2-(5-((2,4,6-trimethoxystyrylsulfonyl)methyl)-2-methoxyphenylamino)propanoate.

B. (E)-2-(5-((2,4,6-Trimethoxystyrylsulfonyl)methyl)-2-methoxyphenylamino)propanoic acid To a solution of methyl(E)-2-(5-((2,4,6-trimethoxystyrylsulfonyl)methyl)-2-methoxyphenylamino)propanoate (0.1 mol) in ethanol (200 mL), was added sodium hydroxide (20% aqueous solution, 200 mL). The resulting mixture was heated at reflux for 2.5 h. The reaction was monitored by TLC. When the reaction was complete, the volatiles were removed under vacuum and the resulting residue was acidified to pH 4 by addition of acetic acid. A solid precipitate formed. The precipitate was separated by filtration. The filtered solid was recrystallized twice from acetone to provide the desired (E)-2-(5-((2,4,6-trimethoxystyrylsulfonyl)methyl)-2-methoxyphenylamino)propanoic acid. m.p. 176-180° C.

Example 4

Synthesis of (E)-5-((2,4,6-trimethoxystyrylsulfonyl)methyl)-2-methoxyphenol

A. 3-O-tert-Butyldimethylsilyloxy-4-methoxybenzaldehyde

To a cooled (0° C.) solution of 3-hydroxy-4-methoxybenzaldehyde (10 g, 65.7 mmol, 1 eq.) in dry N,N-dimethylformamide (75 mL) was added N,N-diisopropylethylamine (16.99 g, 131.4 mmol, 2 eq.). The mixture was stirred under nitrogen for 10 min. A 1.0 M solution of tert-butyldimethylsilylchloride in tetrahydrofuran (78.9 mL, 1.2 eq.) was added dropwise over 30 min. The resulting mixture was stirred 12-16 h and monitored by TLC. When the reaction was complete, water (75 mL) was added to the reaction mixture. The resulting mixture was extracted with dichloromethane (3×75 mL). The combined organic layer was washed with saturated aqueous sodium bicarbonate (75 mL) and water (75 mL) and dried (sodium sulfate). Volatile components were removed in vacuo to yield the crude product. The crude product was purified by column chromatography on silica eluted with chloroform to afford 26.75 g of the product, 3-O-tert-butyldimethylsilyloxy-4-methoxybenzaldehyde, as a yellow oil.

B. 3-O-tert-Butyldimethylsilyloxy-4-methoxybenzyl alcohol

To a cooled (0° C.) solution of 3-O-tert-butyldimethylsilyloxy-4-methoxybenzaldehyde (13 g, 48.8 mmol, 1 eq.) in methanol (100 mL) under nitrogen, was added sodium borohydride (1 eq.). The resulting mixture was allowed to warm to room temperature and stirred (30 min.) and monitored by TLC. When the reduction was complete, water-ice was added to the reaction mixture. The resulting mixture was extracted with ethyl acetate (3×50 mL). The combined organic extract was washed with water (50 mL) and dried (sodium sulfate). Volatile components were removed in vacuo to afford a 73.5% yield of the desired product, 3-O-tert-butyldimethylsilyloxy-4-methoxybenzyl alcohol.

C. 3-O-tert-Butyldimethylsilyloxy-4-methoxy benzyl chloride

To a cooled (0° C.) solution of 3-O-tert-butyldimethylsilyloxy-4-methoxy benzyl alcohol (9.5 g, 35.4 mmol, 1 eq.) in benzene (50 mL) under nitrogen, was added thionyl chloride (6.32 g, 1.5 eq.) dissolved in benzene (5 mL) dropwise over 10 min. The resulting mixture was stirred at 0° C. and monitored by TLC. When the reaction was complete, water ice (50 g) was added and the resulting mixture was extracted with ethyl acetate (3×50 mL). The combined organic extract was washed with saturated bicarbonate solution (50 mL) and water (50 mL) and dried (sodium sulfate). Volatile components were removed in vacuo to afford a quantitative yield of the product 3-O-tert-butyldimethylsilyloxy-4-methoxybenzyl chloride as a yellow oil.

D. 2-((3-O-tert-Butyldimethylsilyloxy-4-methoxybenzyl)sulfanyl)acetic acid

To a solution of sodium hydroxide (2.79 g, 69.7 mmol, 2 eq.) in methanol (30 mL) was added mercaptoacetic acid (3.21 g, 34.9 mmol, 1 eq.) dropwise over 10 min. 3-O-tert-Butyldimethylsilyloxy-4-methoxy benzyl chloride was added portion-wise to the mercaptoacetic acid mixture and the resulting mixture was stirred at room temperature and monitored by TLC. When the reaction was complete, the reaction mixture was poured onto ice (100 mL) containing concentrated hydrochloric acid (excess based on sodium hydroxide). The resulting mixture was extracted with ethyl acetate (3×50 mL). The combined organic extract was washed with water (30 mL) and dried ($Na_2SO_4$). Volatile components were removed in vacuo to afford a 75% yield of the desired product 2-((3-O-tert-butyldimethylsilyloxy-4-methoxybenzyl)sulfanyl)acetic acid as a solid. m.p. of 57-59° C.

E. 2-((3-Hydroxy-4-methoxybenzyl)sulfanyl)acetic acid

To a cooled (0° C.) solution of 2-((3-O-tert-butyldimethylsilyloxy-4-methoxybenzyl)sulfanyl)acetic acid (8.75 g, 25.5 mmol, 1 eq.) in tetrahydrofuran (40 mL) was added dropwise, tetra-n-butylammonium fluoride (1 eq., 1 M in tetrahydrofuran). The resulting mixture was stirred under nitrogen at room temperature and monitored by TLC. When the reaction was complete, water (40 mL) was added to the reaction mixture. The resulting mixture was extracted with ethyl acetate (3×40 mL). The combined organic extract was washed with water (40 mL) and dried (sodium sulfate). Volatile components were removed in vacuo to yield the crude product, which was purified by column chromatography to afford a 50% yield of the purified product, 2-((3-hydroxy-4-methoxybenzyl)sulfanyl)acetic acid.

F. 2-((3-Hydroxy-4-methoxybenzyl)sulfonyl)acetic acid

To a solution of 2-((3-hydroxy-4-methoxybenzyl)sulfanyl) acetic acid (2.9 g) in glacial acetic acid (15 mL) was added hydrogen peroxide (6 mL, 30% solution). The resulting mixture was stirred overnight at room temperature and monitored by TLC. When the reaction was complete, the reaction mixture was poured into ice water (10 mL) and extracted with ethyl acetate (3×10 mL). The combined organic extract was washed with water (10 mL) and dried (sodium sulfate). Volatile components were removed in vacuo to afford a 60% yield of the pure product 2-((3-hydroxy-4-methoxybenzyl)sulfonyl)acetic acid. m.p. 164-165° C.

G. (E)-5-((2,4,6-trimethoxystyrylsulfonyl)methyl)-2-methoxyphenol

A mixture of the 2-((3-hydroxy-4-methoxybenzyl)sulfonyl)acetic acid (1.9 g, 7.3 mmol, 1 eq), 2,4,6-trimethoxybenzaldehyde (1.58 g, 8.0 mmol, 1.1 eq.), benzoic acid (134 mg, 0.15 eq.) and piperidine (81 mg, 0.13 eq.) in toluene (50 mL) was heated at reflux temperature for 2-3 h with continuous removal of water using a Dean-Stark trap. When the reaction was complete by TLC analysis, the reaction mixture was cooled to room temperature. Water was added and the resulting mixture was extracted with ethyl acetate (3×50 mL). The combined organic extract was washed with saturated aqueous sodium bicarbonate solution (50 mL), dilute hydrochloric acid (50 mL), and water (50 mL) and dried (sodium sulfate). Volatile components were removed in vacuo to yield the crude product, which was purified by recrystallization from isopropanol to yield 1.8 g (62.5%) of the desired (E)-5-((2,4,6-trimethoxystyryl-sulfonyl)methyl)-2-methoxyphenol.

Example 5

(E)-2-(5-((2,4,6-Trimethoxystyrylsulfonyl)methyl-2-methoxyphenylamino)acetic acid sodium salt (E)-2-(5-((2,4,6-Trimethoxystyrylsulfonyl)methyl)-2-methoxyphenylamino)acetic acid (15 g, 0.032 mol) is dissolved in ethanol (150 ml) and 1 N NaOH (1.28 g in 33 ml of water, 0.032 mol) is added, adjusted pH to 7.5-8.0 and stirred at room temperature for 1 h. The reaction is cooled to 0° C., and the precipitated solid is collected by filtration, washed with cold ethanol, and finally with hexane and dried under vacuum to give (E)-2-(5-((2,4,6-trimethoxystyrylsulfonyl)methyl)-2-methoxyphenylamino)acetic acid sodium salt (13 g, 84%).

Example 6

Treatment of BEL-7402 Tumor Cells in Nude Mouse Showing a Synergistic Effect of (E)-2-(5-((2,4,6-trimethoxystyrylsulfonyl)methyl)-2-methoxyphenylamino)acetic Acid Sodium Salt and Oxaliplatin A. Procedure Twenty female athymic nude mice (NCR-nu/nu, Taconic) were injected subcutaneously with $1 \times 10^7$ BEL-7402 tumor cells (human hepatoma cell line). The tumors produced by the tumor cell injections were allowed to grow for a period of 10-14 days until the tumors reached a size from 200 to 250 $mm^3$. The mice were then divided into four test groups (N=5) which were treated every other day by intraperitoneal (IP) injections of: (a) (E)-2-(5-((2,4,6-trimethoxystyrylsulfonyl)methyl)-2-methoxyphenylamino)acetic acid sodium salt (Compound A) (200 mg/kg) dissolved in PBS; (b) oxaliplatin (5 mg/kg); (c) a combination of (E)-2-(5-((2,4,6-trimethoxystyrylsulfonyl)methyl)-2-methoxyphenylamino)acetic acid sodium salt (200 mg/kg) dissolved in PBS and oxaliplatin (5 mg/kg), or (d) PBS vehicle containing no drug. The tumor volumes and body weights were determined every seven days and the animals were observed for signs of toxicity. Body weights are plotted in FIG. 1(b) as the mean of the measured weights of all the animals in each dose group. Tumor volume was determined by measuring each tumor in two dimensions using traceable digital Vernier calipers (Fisher Scientific International Inc., Liberty Lane, Hampton, N.H. 03842). The tumor volume was calculated for each tumor using the equation: $V=L \times (S^2)\pi/6$, wherein L is the longer, and S is the shorter of the two measured dimensions. The tumor volume is plotted in FIG. 1(a) as the mean tumor volume±standard error of the mean (SEM) for all animals in each particular dose group.

B. Results

Figure 1B:
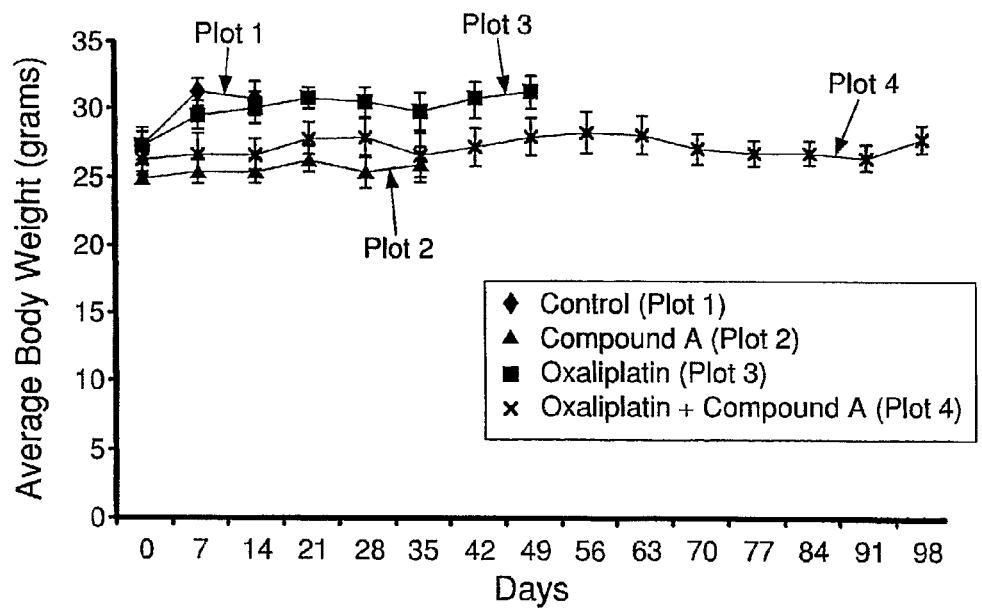
FIG. 1(b) is a plot of the mean body weight of the mice dosed with (i) Compound A (200 mg/kg) (▲), (ii) oxaliplatin (5 mg/kg) (■), (iii) a combination of Compound A (200 mg/kg) and oxaliplatin (5 mg/kg) (✖), or (iv) PBS vehicle (♦) in the same experiment.

As depicted in FIG. 1(a), (E)-2-(5-((2,4,6-trimethoxystyrylsulfonyl)methyl)-2-methoxyphenylamino)acetic acid sodium salt alone or oxaliplatin alone both provided a significant greater reduction in tumor growth. However treatment with the combination of oxaliplatin and (E)-2-(5-((2,4,6-trimethoxystyrylsulfonyl)methyl)-2-methoxyphenylamino) acetic acid sodium salt produced a synergistic effect resulting in complete disappearance of the tumor mass for animals in the dosing group receiving the combination therapy. In addition, there was no evidence of toxicity as assessed by the body weight data shown in FIG. 1(b).

Example 7

Treatment of DU145 Tumor Cells in Nude Mouse Showing a Synergistic Effect of (E)-2-(5-((2,4,6-trimethoxystyrylsulfonyl)methyl)-2-methoxyphenylamino)acetic Acid Sodium Salt and Oxaliplatin A. Procedure Twenty female athymic nude mice (NCR-nu/nu) were injected subcutaneously with $1.0 \times 10^7$ DU145 tumor cells (human prostate cancer cell line). Tumor growth was monitored by measurements using a Vernier caliper and the tumors were allowed to grow until an average volume of 600 $mm^3$ had been reached. At this time, animals were divided into four groups (N=5) and were treated every other day by IP injections with: (a) (E)-2-(5-((2,4,6-trimethoxystyrylsulfonyl)methyl)-2-methoxyphenylamino)acetic acid sodium salt (200 mg/kg) dissolved in PBS; (b) oxaliplatin (5.0 mg/kg); (c) a combination of (E)-2-(5-((2,4,6-trimethoxystyrylsulfonyl)methyl)-2-methoxyphenylamino)acetic acid sodium salt (200 mg/kg) dissolved in PBS and oxaliplatin (5.0 mg/kg); and (d) PBS vehicle containing no drug. All animals were examined for signs of toxicity. Tumor volumes and body weights were determined weekly. Tumor volume was determined by measuring each tumor in two dimensions using traceable digital Vernier calipers. The tumor volume was calculated for each tumor using the equation: $V=L \times (S^2)\pi/6$. The tumor volumes were determined for 105 days, in the combination group, or until the animal was sacrificed or found dead. The tumor volume is plotted in FIG. 2 as the mean tumor volume±standard error of the mean (SEM) for all animals in each particular dose group.

B. Results

As depicted in FIG. 2, the animals treated with single agents, either (E)-2-(5-((2,4,6-trimethoxystyrylsulfonyl)methyl)-2-methoxyphenylamino)acetic acid sodium salt or oxaliplatin, had a significant therapeutic response and a tumor growth delay, time required for treated tumors to increase to size of control tumors, of greater than 35 days. Treatment of tumor-bearing mice with of (E)-2-(5-((2,4,6-trimethoxystyrylsulfonyl)methyl)-2-methoxyphenylamino)acetic acid sodium salt in combination with oxaliplatin resulted in a significant synergistic reduction in tumor growth. The average tumor volume was reduced to below the starting volume after 28 days of treatment and the tumors never reached the maximum tumor volumes, observed in the control treated mice, even after 105 days. In addition, the tumor volumes of the combination group never reached the tumor volumes observed in either of the animals treated with either (E)-2-(5-((2,4,6-trimethoxystyrylsulfonyl)methyl)-2-methoxyphenylamino)acetic acid sodium salt or oxaliplatin alone. The time of tumor volume doubling was approximately 9 days for the control group, approximately 25 days for the single agent treated groups and approximately 75 days for the mice treated with the combination therapy.

Example 8

Treatment of MCF-7 Tumor Cells in Nude Mouse Showing a Synergistic Effect of (E)-2-(5-((2,4,6-trimethoxystyrylsulfonyl)methyl)-2-methoxyphenylamino)acetic Acid Sodium Salt and Doxorubicin A. Procedure Estradiol pellets (1 mg) were implanted interscapularly into twenty female athymic nude mice (NCR-nu/nu, Taconic) mouse. After 24 hours $1 \times 10^7$ MCF-7 tumor cells (breast cancer cell line) were implanted in the mammary fat pad of each mouse. The tumors produced by the tumor cell injections were allowed to grow for a period of 10-15 days until the tumors reached a size from 200 to 250 mm$^3$. The mice were then divided into four test groups (N=5) which were treated every other day by IP injections with: (a) (E)-2-(5-((2,4,6-trimethoxystyrylsulfonyl)methyl)-2-methoxyphenylamino) acetic acid sodium salt (200 mg/kg) dissolved in PBS; (b) doxorubicin (2.5 mg/kg) dissolved in PBS; (c) a combination of (E)-2-(5-((2,4,6-trimethoxystyrylsulfonyl)methyl)-2-methoxyphenylamino)acetic acid sodium salt (200 mg/kg) and doxorubicin (2.5 mg/kg) dissolved in PBS; or (d) PBS vehicle containing no drug. The tumor volumes and body weights were determined every seven days and the animals were observed for signs of toxicity. Body weights are plotted in FIG. 3(b) as the mean of the measured weights of all the animals in each dose group. Tumor volume was determined by measuring each tumor in two dimensions using traceable digital Vernier calipers. The tumor volume was calculated for each tumor using the equation: $V=L \times (S^2) \pi/6$. The tumor volume is plotted in FIG. 3(a) as the mean tumor volume all animals in each particular dose group.

B. Results

Figure 3A:
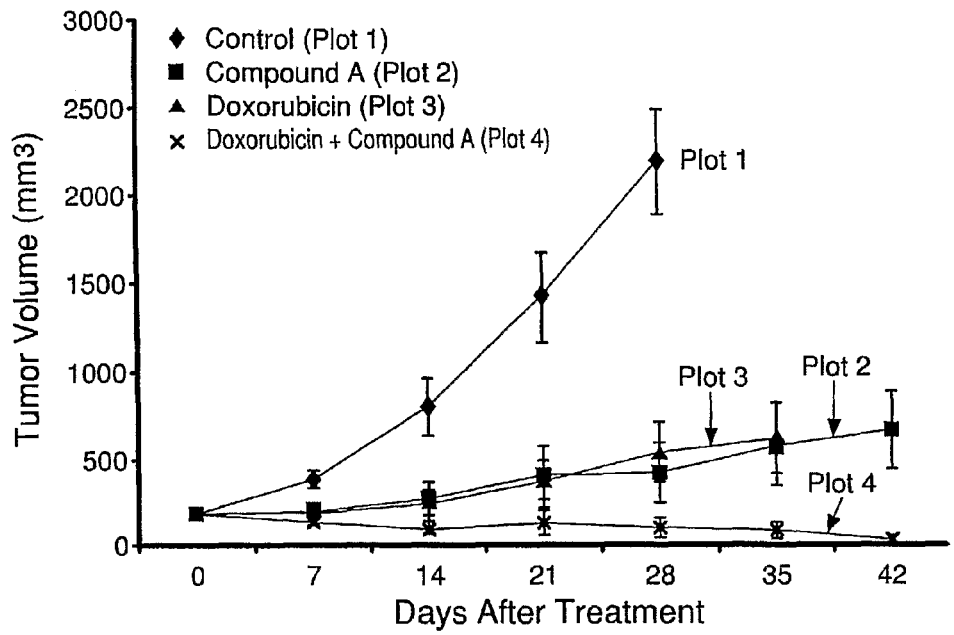
FIG. 3(a) is a graph of the effect of the intraperitoneal administration of (i) the compound of Compound A (200 mg/kg) (■), (ii) doxorubicin (2.5 mg/kg) (▲), (iii) a combination of Compound A (200 mg/kg) and doxorubicin (2.5 mg/kg) (✖) or (iv) PBS vehicle (♦), on in vivo growth of MCF-7 tumor cells (human breast cancer cell line) in nude mice following subcutaneous injection of $1\times10^7$ of the cells.
Figure 3B:
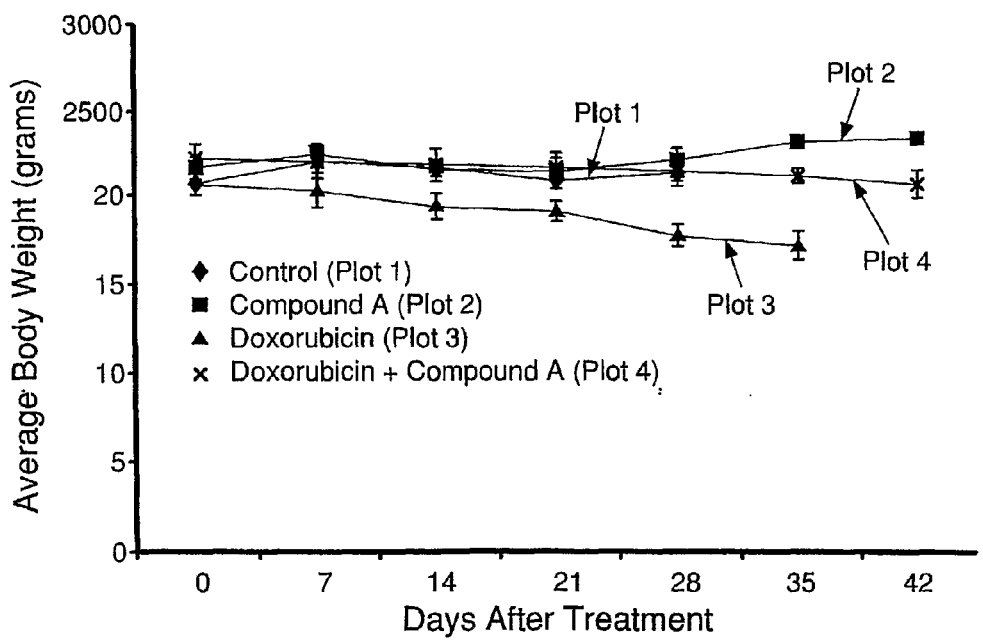
FIG. 3(b) is a plot of the mean body weight of the mice dosed with (i) the compound of Compound A (200 mg/kg) (■), (ii) doxorubicin (2.5 mg/kg) (▲), (iii) a combination of Compound A (200 mg/kg) and doxorubicin (2.5 mg/kg) (✖) or (iv) PBS vehicle (♦) in the same experiment.

As depicted in FIG. 3(a), (E)-2-(5-((2,4,6-trimethoxystyrylsulfonyl)methyl)-2-methoxyphenylamino)acetic acid sodium salt alone provided a comparable reduction in tumor growth than treatment with doxorubicin. By the 35$^{th}$ day, all the doxorubicin animals had died, despite the fact their tumors were only 500 mm$^3$ whereas all animals treated with (E)-2-(5-((2,4,6-trimethoxystyrylsulfonyl)methyl)-2-methoxyphenylamino)acetic acid sodium salt (200 mg/kg) alone survived to 84 days. However, treatment with the combination of doxorubicin and (E)-2-(5-((2,4,6-trimethoxystyrylsulfonyl)methyl)-2-methoxyphenylamino)acetic acid sodium salt produced a synergistic effect resulting in complete disappearance of the tumor mass for animals in the dosing group receiving the combination therapy. In addition, there was no evidence of toxicity as assessed by the body weight data shown in FIG. 3(b).

Example 9

Treatment of MCF-7 Tumor Cells in Nude Mouse Showing that (E)-2-(5-((2,4,6-trimethoxystyrylsulfonyl)methyl)-2-methoxyphenylamino)acetic Acid Sodium Salt Ameliorates the Toxic and Lethal Effects of Doxorubicin A. Procedure Estradiol pellets (1 mg) were implanted interscapularly into ten female athymic nude mice (NCR-nu/nu, Taconic) mouse. After 24 hours $1 \times 10^7$ MCF-7 tumor cells were implanted in the mammary fat pad of each mouse. The tumors produced by the tumor cell injections were allowed to grow for a period of 10-15 days until the tumors reached a size from 200 to 250 mm$^3$. The mice were then divided into two test groups (N=5) which were treated by IP injections every other day with: (a) doxorubicin (1.0 mg/kg dissolved in PBS); or (b) a combination of (E)-2-(5-((2,4,6-trimethoxystyrylsulfonyl)methyl)-2-methoxyphenylamino)acetic acid sodium salt (200 mg/kg) and doxorubicin (1.0 mg/kg dissolved in PBS). The body weights were determined every seven days and the animals were observed for signs of toxicity. Body weights for the individual animals of group (a) are plotted in FIG. 4(a) and body weights for the individual animals of group (b) are plotted in FIG. 4(b).

B. Results

Figure 4A:
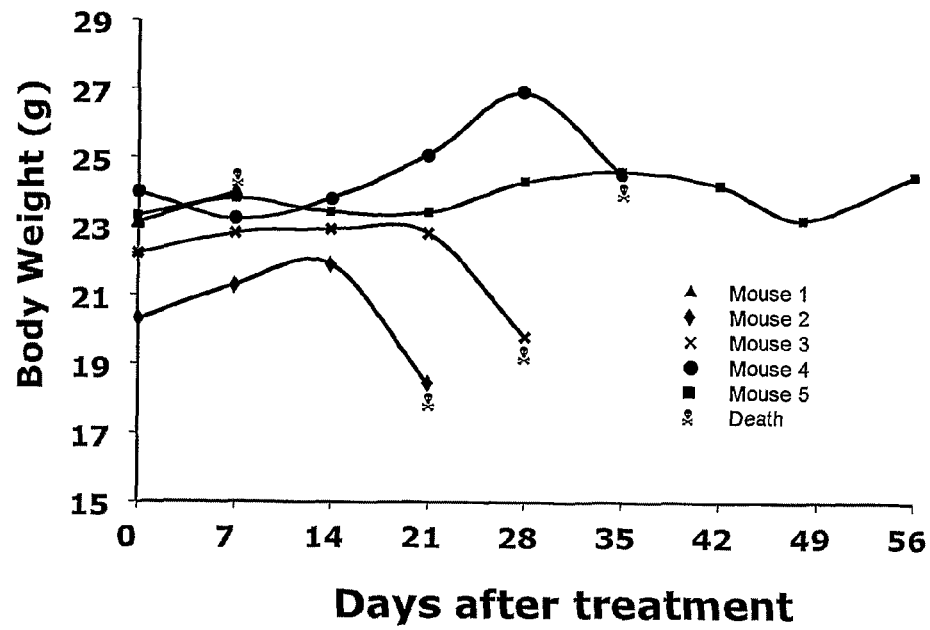
FIG. 4(a) is a plot of the body weight of individual nude mice which were injected with dosed subcutaneously with $1\times10^7$ MCF-7 tumor cells and dosed with doxorubicin (1.0 mg/kg). The weight of the mice was recorded weekly until the mice died (as indicated by the symbol ☒).
Figure 4B:
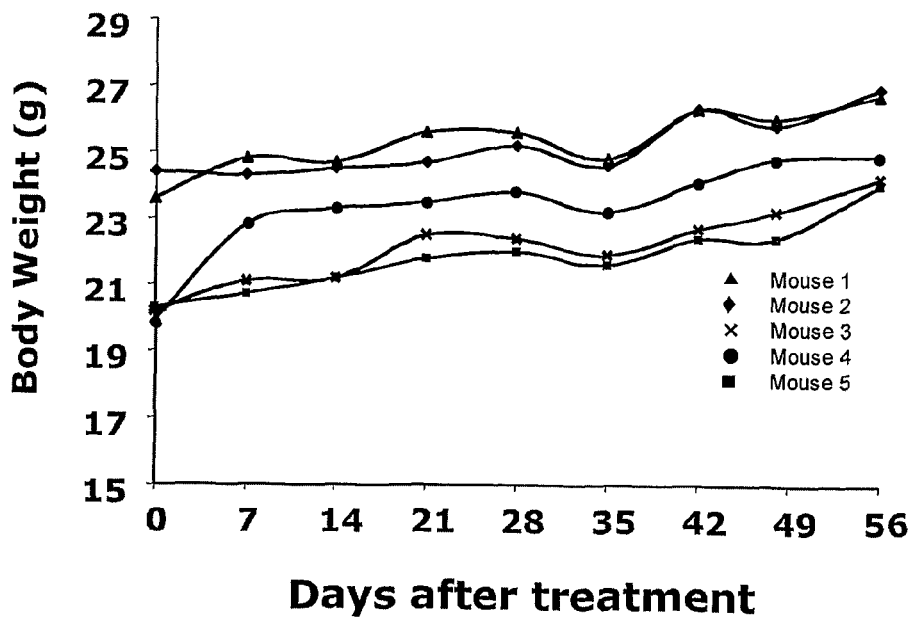
FIG. 4(b) is a plot of the body weight of identically treated nude mice dosed with a combination of Compound A (200 mg/kg) and doxorubicin (1.0 mg/kg).

In FIG. 4(a), animals of group (a) receiving doxorubicin at 1 mg/kg intraperitoneally every other day showed initial suggestive weight gain, but a high proportion of the animals died. Major weight loss immediately preceding death occurred in 4 of the 5 animals (as indicated in FIG. 4(a) by the symbol ✱). In contrast, as shown in FIG. 4(b), animals of group (b) receiving the same doxorubicin dose plus (E)-2-(5-((2,4,6-trimethoxystyrylsulfonyl)methyl)-2-methoxyphenylamino) acetic acid sodium salt (200 mg/kg) all survived for 56 days, and all moderately gained weight.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A composition comprising (E)-2-(5-((2,4,6-trimethoxystyrylsulfonyl)methyl)-2-methoxyphenylamino)acetic acid or a pharmaceutically acceptable salt thereof, and at least one chemotherapeutic agent selected from the group consisting of oxaliplatin, doxorubicin, and pharmaceutically acceptable salts thereof.

2. A composition according to claim 1, wherein the at least one chemotherapeutic agent is doxorubicin, or a pharmaceutically acceptable salt thereof.

3. A composition according to claim 1, wherein the at least one chemotherapeutic agent is oxaliplatin.

4. A composition according to claim 1, comprising a sodium salt of (E)-2-(5-((2,4,6-trimethoxystyrylsulfonyl) methyl)-2-methoxyphenylamino)acetic acid.

5. A method of treating an individual for a cancer comprising administering to the individual an effective amount of at least one composition according to claim 1.

6. A method of treating an individual for a cancer comprising administering to the individual an effective amount of at least one composition according to claim 2.

7. A method according to claim 5, wherein the cancer is selected from the group consisting of ovarian cancer, cervical cancer, breast cancer, liver cancer, prostate cancer, testicular cancer, lung cancer, renal cancer, colorectal cancer, skin cancer, brain cancer and leukemia.

8. A method of treating an individual for a cancer comprising administering to the individual an effective amount of at least one composition according to claim 3.

9. A method of treating an individual for a cancer proliferative disorder comprising administering to the individual an effective amount of (E)-2-(5-((2,4,6-trimethoxystyrylsulfonyl)methyl)-2-methoxyphenylamino)acetic acid or a pharmaceutically acceptable salt thereof; and an effective amount of at least one chemotherapeutic agent selected from the group consisting of oxaliplatin, doxorubicin, and pharmaceutically acceptable salts thereof.

10. A method according to claim 9, wherein the at least one chemotherapeutic agent is doxorubicin, or a pharmaceutically acceptable salt thereof.

11. A method according to claim 9, wherein the at least one chemotherapeutic agent is oxaliplatin.

12. A method according to claim 9, comprising administering to a to the individual an effective amount of a sodium salt of (E)-2-(5-((2,4,6-trimethoxystyrylsulfonyl)methyl)-2-methoxyphenylamino)acetic acid.

13. A method according to claim 9, wherein the cancer is selected from the group consisting of ovarian cancer, cervical cancer, breast cancer, liver cancer, prostate cancer, testicular cancer, lung cancer, renal cancer, colorectal cancer, skin cancer, brain cancer and leukemia.

14. A kit comprising, in a first compartment, (E)-2-(5-((2,4,6-trimethoxystyrylsulfonyl)methyl)-2-methoxyphenylamino)acetic acid or a pharmaceutically acceptable salt thereof; and, in a second compartment, a chemotherapeutic agent selected from the group consisting of oxaliplatin, doxorubicin, and pharmaceutically acceptable salts thereof.

15. A kit according to claim 14, wherein the at least one chemotherapeutic agent is doxorubicin, or a pharmaceutically acceptable salt thereof.

16. A kit according to claim 14, wherein the at least one chemotherapeutic agent is oxaliplatin.

17. A kit according to claim 14, comprising a sodium salt of (E)-2-(5-((2,4,6-trimethoxystyrylsulfonyl)methyl)-2-methoxyphenylamino)acetic acid in the first compartment.

18. The method according to claim 9 wherein the (E)-2-(5-((2,4,6-trimethoxystyrylsulfonyl)methyl)-2-methoxyphenylamino)acetic acid or pharmaceutically acceptable salt thereof and the at least one chemotherapeutic agent are administered concomitantly.

* * * * *